United States Patent
Nørregaard-Madsen et al.

(10) Patent No.: US 6,558,939 B1
(45) Date of Patent: May 6, 2003

(54) PROTEASES AND VARIANTS THEREOF

(75) Inventors: Mads Nørregaard-Madsen, Odense (DK); Peter Rahbek Østergaard, Virum (DK); Claus Bo Vøge Christensen, Snekkersten (DK); Søren Flensted Lassen, København (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/551,826

(22) Filed: Apr. 17, 2000

Related U.S. Application Data

(60) Provisional application No. 60/156,743, filed on Sep. 30, 1999.

(30) Foreign Application Priority Data

Aug. 31, 1999 (DK) ......................................... 1999 01212
Oct. 20, 1999 (DK) ......................................... 1999 01500

(51) Int. Cl.$^7$ .......................... C12N 9/56; C12N 15/57; C12N 15/74; C12N 15/75; C11D 3/386
(52) U.S. Cl. ................... 435/222; 435/69.1; 435/252.3; 435/320.1; 435/471; 536/23.2; 510/350
(58) Field of Search ................................ 435/220, 471, 435/69.1, 252.3, 320.1; 510/350; 536/23.2

(56) References Cited

U.S. PATENT DOCUMENTS

| | | | | |
|---|---|---|---|---|
| 4,266,031 A | | 5/1981 | Tang et al. | 435/188 |
| 5,523,237 A | * | 6/1996 | Budtz et al. | 435/68.1 |
| 5,747,321 A | * | 5/1998 | Yabuta et al. | 435/220 |
| 5,863,573 A | * | 1/1999 | Dambmann et al. | 426/36 |
| 5,866,357 A | * | 2/1999 | Dambmann et al. | 435/68.1 |

FOREIGN PATENT DOCUMENTS

| | | |
|---|---|---|
| EP | 0 130 756 A1 | 1/1985 |
| EP | 0 251 446 B1 | 1/1988 |
| EP | 0 369 817 A2 | 5/1990 |
| EP | 0 482 879 A2 | 4/1992 |
| WO | WO 91/13553 | 9/1991 |
| WO | WO 96/34946 | 11/1996 |

OTHER PUBLICATIONS

Kakudo, S., et al., 1992, "Purification, characterization, cloning, and expression of a glutamic acid-specific protease from *Bacillus licheniformis* ATCC 14580", The Journal of Biological Chemistry, vol. 267, pp. 23782–23788.*

Svendsen, I., and Breddam, K., 1992 "Isolation and amino acid sequence of a glutamic acid specifid endopeptidase from *Bacillus licheniformis*", European Journal of Biochemistry, vol. 304, pp. 165–171.*

Okamoto et al., (1997) Appl. Microbiol. Biotechnol. 48:27–33.

Rufo, Jr. et al., (1990) J. Bacteriology p. 1019–1023.

Sloma et al., (1990) J. Bacteriology p. 1024–1029.

Siezen et al., (1997) Protein Science 6:501–523.

* cited by examiner

*Primary Examiner*—Ponnathapu Achuthamurthy
*Assistant Examiner*—William W. Moore
(74) *Attorney, Agent, or Firm*—Elias J. Lambiris

(57) ABSTRACT

Novel isolated proteases of the RP-II type and variants of RP-II proteases exhibiting improved properties in comparison to the parent RP-II protease, DNA constructs and vectors coding for the expression of said proteases and variants, host cells capable of expressing the proteases and variants from the DNA constructs, as well as a method of producing them by cultivating said host cells. The proteases may advantageously be used as constituents in detergent compositions and additives, optionally in combination with other enzymes such as proteases, lipases, cellulases, amylase, peroxidases or oxidases.

27 Claims, 5 Drawing Sheets a) BLC = RP-II protease from *Bacillus licheniformis*,
b) AA513 = RP-II protease from *Bacillus sp. AC116*
c) AC116 = RP-II protease from *Bacillus sp. AC116*
d) BO32 = RP-II protease from *Bacillus sp. AC116*
e) CDJ31 = RP-II protease from *Bacillus sp. AC116*
f) JA96 = RP-II protease from *Bacillus sp. AC116*
g) MPR = RP-II protease from *Bacillus subtilis*

```
a)   1 SVIGSDDRTRVTNTTAYPYRAIVHIS....SSIGSCTGWMIGPKTVATAG  46
b)     VVIGDDGRRQVQNTSFMPFRALTYIEFGNLTSTWSCSGGVIGTDLVVTNA a)  47 HCIYDTSSGSFAGTATVSPGRNGTSYPYGSVKSTRYFIPSGWR.SGNTNY  95
b)     HCV....EGSVL.AGTVVPGMNNSQWAYGHYRVTQIIYPDQYRNNGASEF a)  96 DYGAIELS.....EPIGNTVGYFGYSYTTSSLVGTTVTISGYPGDKTAGT 140
b)     DYAILRVAPDSDGRHIGNRAGILSFTETGTVNENTFLRTYGYPGDKISET a) 141 Q....WQHSG.PIAISETYKLQYAMDTYGGQSGSPVFEQSSSRTNCSGPC 185
b)     KLISLWGMVGRSDAFLHRDLLFYNMDTYFGQSGSPVLNSVDSMVAVHNAG a) 186 SLAVHTNGVYGGSSYNRGTRITKEVFDNLTNWKNSAQ 222
b)     YIVGGNREINGGPKIRRDFTNLFNQMN..........

a)   1 SVIGSDDRTRVTNTTAYPYRAIVHISSSIGSCTGWMIGPKTVATAGHCIY  50
c)     SVIGSDERTRVTDTTAFPYRAIVHISSSIGSCTGWLIGPKTVATAGHCVY a)  51 DTSSGSFAGTATVSPGRNGTSYPYGSVKSTRYFIPSGWRSGNTNYDYGAI 100
c)     DTASRSFAGTATVSPGRNGSAYPYGSVTSTRYFIPSGWQSGNSNYDYAAI a) 101 ELSEPIGNTVGYFGYSYTTSSLVGTTVTISGYPGDKTAGTQWQHSGPIAI 150
c)     ELSQPIGNTVGYFGYSYTASSLAGAGVTISGYPGDKTTGTQWQMSGTIAV a) 151 SETYKLQYAMDTYGGQSGSPVFEQSSSRTNCSGPCSLAVHTNGVYGGSSY 200
c)     SETYKLQYAIDTYGGQSGSPVYEKSSSRTNCSGPCSLAVHTNGVYGGSSY a) 201 NRGTRITKEVFDNLTNWKNSAQ 222
c)     NRGTRITKEVFDNFTSWKNSAQ 222
```

Fig. 1a

```
a)    1  SVIGSDDRTRVTNTTAYPYRAIVHISSSIGSCTGWMIGPKTVATAGHCIY  50
d)       VVIGDDGRTKVANTRVAPYNSIAYTTFGGSSCTGTLIAPNKILTNGHCVY a)   51  DTSSGSFAGTATVSPGRNGTSYPYGSVKSTRYFIPSGW.RSGNTNYDYGA  99
d)       NTASRSYSAKGSVYPGMNDSTAVNGSANMTEFYVPSGYINTGASQYDFAV a)  100  IELSEPIGNTVGYFGYSYTTSSLVGTTVTISGYPGDKTAGT....QWQHS 145
d)       IKTDTNIGNTVGYRSIRQVT.NLTGTTIKISGYPGDKMRSTGKISQWEMS a)  146  GPIAISETYKLQYAMDTYGGQSGSPVFEQSSSRTNC.SGPCSLAVHTNGV 194
d)       GPVTREDTNLAYYMIDTFSGNSGSAMLDQNQQIVGVHNAGYSNGTINGGP a)  195  YGGSSYNRGTRITKEVFDNLTNWKNSAQ 222
d)       KATAAFVEFINYAKAQ............

a)    1  SVIGSDDRTRVTNTTAYPYRAIVHISSSIGSCTGWMIGPKTVATAGHCIY  50
e)       SVIGSDERTRVTNTTAYPYRAIVHISSSIGSCTGSLIGPKTVATAGHCIY a)   51  DTSSGSFAGTATVSPGRNGTSYPYGSVKSTRYFIPSGWRSGNTNYDYGAI 100
e)       DTASGSFAGTATVSPGRNGSTYPYGSVTSTRYFIPSGYRSGNSNYDYGAI a)  101  ELSEPIGNTVGYFGYSYTTSSLVGTTVTISGYPGDKTAGTQWQHSGPIAI 150
e)       ELSQPIGNTVGYFGYSYTTSSLVGSSVTIIGYPGDKTSGTQWQMSGNIAV a)  151  SETYKLQYAMDTYGGQSGSPVFEQSSSRTNCSGPCSLAVHTNGVYGGSSY 200
e)       SETYKLQYAIDTYGGQSGSPVYEASSSRTNCSGPCSLAVHTNGVYGGSSY a)  201  NRGTRITKEVFDNLTNWKNSAQ 222
e)       NRGTRITKEVFDNLTNWKNSAQ a)    1  SVIGSDDRTRVTNTTAYPYRAIVHISSSIGSCTGWMIGPKTVATAGHCIY  50
f)       VVIGDDGRTKVTNTRVAPYNSIAYITFGGSSCTGTLIAPNKILTNGHCVY a)   51  DTSSGSFAGTATVSPGRNGTSYPYGSVKSTRYFIPSGW.RSGNTNYDYGA  99
f)       NTATRSYSAKGSVYPGMNDSTAVNGSANMTEFYVPSGYINTGASQYDFAV a)  100  IELSEPIGNTVGYFGYSYTTSSLVGTTVTISGYPGDKTAGT....QWQHS 145
f)       IKTDTNIGNTVGYRSIRQVT.NLTGTTIKISGYPGDKMRSTGKVSQWEMS a)  146  GPIAISETYKLQYAMDTYGGQSGSPVFEQSSSRTNC.SGPCSLAVHTNGV 194
f)       GPVTREDTNLAYYTIDTFSGNSGSAMLDQNQQIVGVHNAGYSNGTINGGP a)  195  YGGSSYNRGTRITKEVFDNLTNWKNSAQ 222
f)       KATAAFVEFINYAKAQ............
```

Fig. 1b

```
a)    1  SVIGSDDRTRVTNTTAYPYRAIVHIS......SSIGSCTGWMIGPKTVAT  44
g)       SIIGTDERTRISSTTSFPYRATVQLSIKYPNTSSTYGCTGFLVNPNTVVT a)   45  AGHCIYDTSSGSFAGTATVSPGRNGTSYPYGSVKSTRYFIPSGW.RSGNT  93
g)       AGHCVYSQDHG.WASTITAAPGRNGSSYPYGTYSGTMFYSVKGWTESKDT a)   94  NYDYGAIELSEPIGNTVGYFGYSYT.TSSLVGTTVTISGYPGDKTAGTQW 142
g)       NYDYGAIKLNGSPGNTVGWYGYRTTNSSSPVGLSSSVTGFPCDKTFGTMW a)  143  QHSGPIAISETYKLQYAMDTYGGQSGSPVFEQSSSRTNCSGPCSLAVHTN 192
g)       SDTKPIRSAETYKLTYTTDTYGCQSGSPVYRNYSD....TGQTAIAIHTN a)  193  GVYGGSSYNRGTRITKEVFDNLTNWKNSAQ 222
g)       ...GGSSYNLGTRVTNDVFNNIQYWANQ..
```

Fig. 1c

PROTEASES AND VARIANTS THEREOF

CROSS REFERENCE TO RELATED APPLICATIONS

This application claims priority under 35 U.S.C. 119 of Danish applications PA 1999 01212 filed Aug. 31, 1999 and PA 1999 01500 filed Oct. 20, 1999, and of U.S. Provisional application No. 60/156,743 filed Sep. 30, 1999, the contents of which are fully incorporated herein by reference.

FIELD OF THE INVENTION

The present invention relates to novel isolated proteases of the RP-II type and variants of RP-II proteases exhibiting improved properties in comparison to the parent RP-II protease, DNA constructs and vectors coding for the expression of said proteases and variants, host cells capable of expressing the proteases and variants from the DNA constructs, as well as a method of producing them by cultivating said host cells. The proteases may advantageously be used as constituents in detergent compositions and additives.

BACKGROUND OF THE INVENTION

Proteases of the subtilisin family (Siezen et al. *Protein Science* 6 (1997) 501–523) have for many years been used in the detergent industry due to their apparent superiority over other protease types in this type of application.

A large number of subtilisins and the related subtilases are known.

Protease variants have been produced in a number of subtilisin proteases in order to provide changes in various properties, such as thermo stability, specific activity, pH-dependency, isoelectric point, wash performance, oxidation stability, autoproteolysis, etc.

Such variants are disclosed in various patent publications, such as EP 130 756, EP 251 446, and EP 824 585.

The fact that novel detergents constantly are being developed to satisfy various user demands provides an incentive to continuously develop novel proteases capable of providing excellent performance in the novel detergents.

Bacillus proteases of the RP-II type are another type of serine proteases that in primary structure are similar to chymotrypsinogen.

The first description of a protease of the RP-II family of Bacillus proteases was in U.S. Pat. No. 4,266,031 (Tang et al., Novo Industri A/S), where it was designated Component C and tentatively characterised as not being a serine protease or metalloprotease. Component C was considered a contaminant in the production of the *Bacillus licheniformis* alkaline protease, subtilisin Carlsberg.

In EP 369 817 (Omnigene Bioproducts, Inc.) the *B. subtilis* member of the RP-II family was identified by its amino acid and DNA sequences. The enzyme was stated not to be a serine protease, and the family name RP-II designated (Residual Protease II). The enzyme was characterised further by the inventors of EP 369 817 in Rufo et al., 1990, *J. Bacteriol.* 2 1019–1023, and Sloma et al., 1990, *J. Bacteriol.* 2 1024–1029, as a metalloprotease designating the enzyme as mpr.

WO 91/13553 (Novo Nordisk A/S) disclosed the amino acid sequence of the C component now stating that it is a serine protease specific for glutamic and aspartic acid, while EP 482 879 (Shionogi & Co. Ltd.) disclosed the enzyme and a DNA sequence encoding the C component from *B. licheniformis* ATCC No. 14580, naming the enzyme BLase. In EP 482 879 the protease is described as being specific for glutamic acid.

In 1997 Okamoto et al. (*Appl. Microbiol. Biotechnol.* (1997) 48 27–33) found that the *B. subtilis* homologue of BLase, named BSase was identical to the above mentioned enzyme, mpr/RP-II.

SUMMARY OF THE INVENTION

Initial testing of the *B. licheniformis* member of the RP-II family had indicated that this enzyme in some aspects may be inferior in detergents in comparison to the subtilisins.

However, it is believed that a screening program for novel RP-II family members both isolated from nature (wild types) and recombinantly produced variants thereof will provide alternative proteases for use in detergents.

Consequently it is an object of the present invention to provide novel RP-II protease members obtainable from various Bacillus strains.

Furthermore it is the object of the present invention to design novel variants of the RP-II proteases having improved properties as compared to those of their parent protease.

Accordingly, in a first aspect the present invention relates to novel isolated RP-II proteases selected from the group consisting of:

(i) a RP-II protease that is immunochemically identical or partially identical by cross-reaction with an antibody raised against or reactive with at least one epitope of a RP-II protease comprising the amino acid sequences of the mature peptides shown in the appended Sequence Listing SEQ ID NO: 2, 4, ID No. 6, ID No. 8, ID No. 10, or ID No. 12; and/or (ii) a RP-II protease that is at least 60% homologous with the amino acid sequence of a RP-II protease comprising the amino acid sequence shown in the appended Sequence Listing SEQ ID NO: 2, SEQ ID NO: 4, SEQ ID NO: 6, SEQ ID NO: 8, SEQ ID NO: 10, or SEQ ID NO: 12; and/or (iiia) a RP-II protease that is encoded by a DNA sequence which hybridizes with an oligonucleotide probe hybridizing with a DNA sequence encoding a RP-II protease comprising the amino acid sequence shown in the appended Sequence Listing SEQ ID NO: 2, SEQ ID NO: 4, SEQ ID NO: 6, SEQ ID NO: 8, SEQ ID NO: 10, or SEQ ID NO: 12; and/or (iiib) a RP-II protease that is encoded by a DNA sequence which hybridizes with an oligonucleotide probe hybridizing with a DNA sequence encoding a RP-II protease comprising the DNA sequence shown in the appended Sequence Listing SEQ ID NO: 1, SEQ ID NO: 3, SEQ ID NO: 5, SEQ ID NO: 7, SEQ ID NO: 9, or SEQ ID NO: 11;

(iv) an allelic variant of (i), (ii), or (iiia or iiib);

(v) a subsequence of (i), (ii), (iiia or iiib), or (iv), wherein the subsequence has protease activity.

The invention furthermore relates to RP-II protease variants produced by modifying at least one amino acid residue within the mature enzyme in order to obtain a modification of the properties of the parent enzyme.

Such variants of the present invention are contemplated to have improved substrate specificities, catalytic rate, stability, especially towards the action of proteolytic enzymes and/or detergent ingredients, thermostability, storage stability, improved resistance towards peroxidase/pHBS inactivation, and/or improved wash performance as compared to the parent RP-II protease. The variants of the invention include fragments of the RP-II proteases or variants thereof having retained protease activity.

The present invention also relates to novel isolated nucleic acid sequences encoding RP-II proteases, selected from the group consisting of:

(a) a nucleic acid sequence having at least 60% homology with the nucleic acid sequence encoding the mature polypeptide of SEQ ID NO: 1, 3, 5, 7, 9, or 11;

(b) a nucleic acid sequence which hybridizes under low stringency conditions with (i) the nucleic acid sequence of SEQ ID NO: 1, 3, 5, 7, 9, or 11 (ii) the cDNA sequence of SEQ ID NO: 1, 3, 5, 7, 9, or 11, (iii) a subsequence of (i) or (ii) of at least 100 nucleotides, or (iv) a complementary strand of (i), (ii), or (iii);

(c) an allelic variant of (a), or (b);

(d) a subsequence of (a), (b), or (c), wherein the subsequence encodes a polypeptide fragment which has protease activity; and The present invention also relates to nucleic acid or DNA constructs comprising a DNA sequence encoding a RP-II protease or RP-II protease variant as indicated above, recombinant expression vectors carrying said DNA construct, cells transformed with a DNA construct or expression vector, as well as methods for producing a RP-II protease or variant of the invention by culturing or growing said cell under conditions conducive to the production of the protease or variant, after which the protease or variant is recovered from the culture, and optionally purified to be substantially pure.

The invention further relates to an enzyme granulate, a liquid enzyme composition or a protected enzyme preparation comprising a RP-II protease or protease variant of the invention and suitable for the preparation of e.g. a detergent composition comprising a RP-II protease or RP-II protease variant of the invention.

Deposited Biological Materials

DNA encoding the novel RP-II proteases of the invention has been inserted into plasmids used to transform *E. coli*. These transformants have been been deposited according to the Budapest Treaty on the International Recognition of the Deposits of Microorganisms for the Purpose of Patent Procedures, on Dec. 3, 1990 at DSMZ-Deutsche Sammlung von Mikroorganismen und Zellkulturen GmbH (DSM), Mascheroder Weg 1b, D-38124 Braunschweig, Germany, under Accession Nos. DSM 12841 (AC116), DSM 12842 (CDJ31), DSM 12843 (BO32), DSM 12844 (JA96), and DSM 12845 (AA519).

The deposits have been made under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

BRIEF DESCRIPTION OF DRAWINGS

The present invention is further illustrated by reference to the accompanying drawings, in which:

FIGS. 1a to 1c shows an alignment of the novel wild type RP-II proteases to the RP-II protease from *Bacillus licheniformis*, BLC, in the manner described below to establish the numbering of the amino acid residues for each novel wild type protease.

DEFINITIONS

Figure 2A:
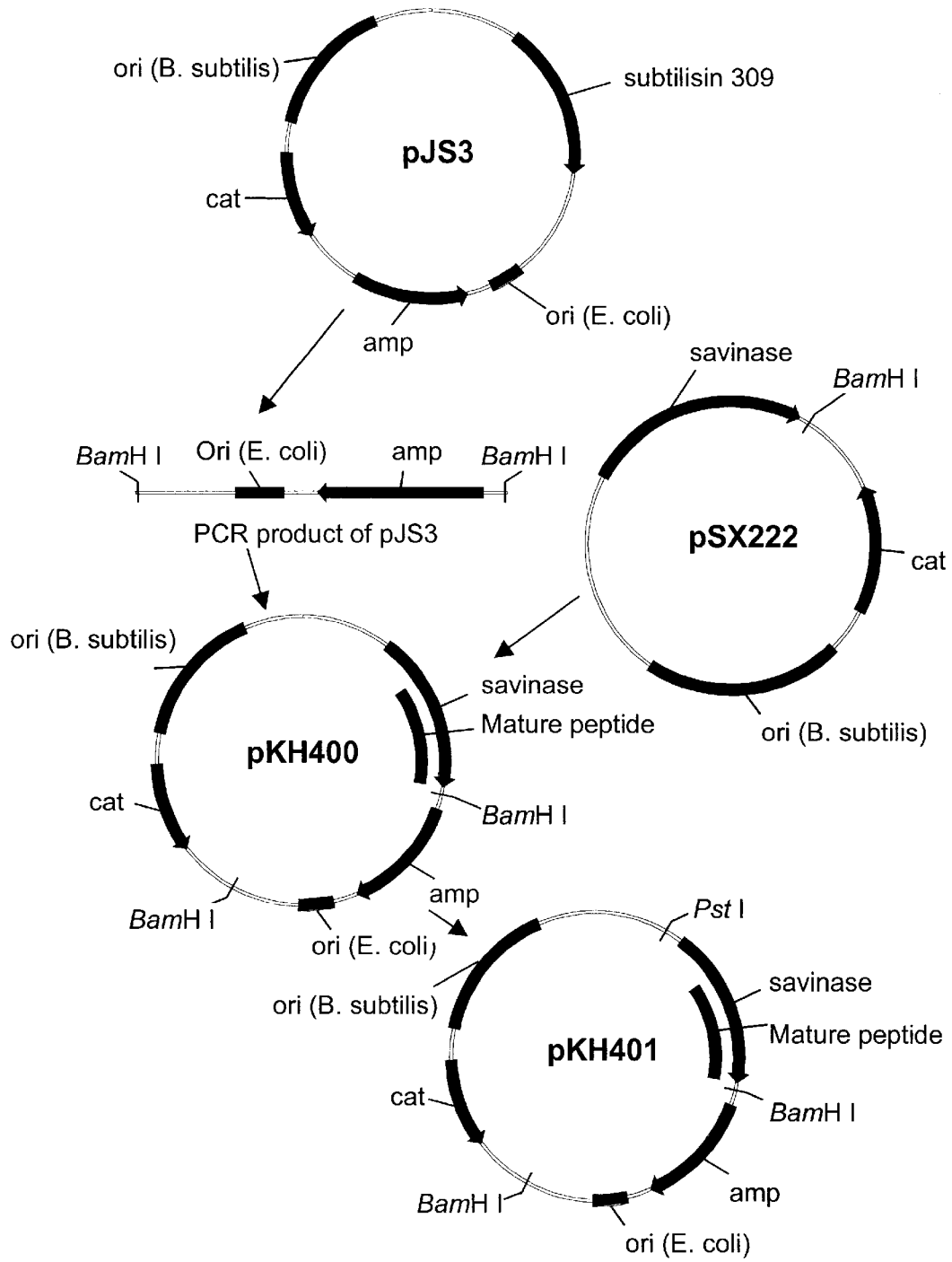
FIGS. 2a and 2b shows schematically the construction of plasmid pNM1003.

In the present context, the term "RP-II protease" is intended to indicate an evolutionary homologue of the RP-II protease derived from a bacterium of the genus Bacillus, and in particular of any of the species *B. licheniformis, B. pumilus, B. subtilis,* or *B. halmapalus* or a functional analogue thereof.

The term "functional analogue" is intended to indicate a RP-II protease which is immunologically cross-reactive with at least one of the RP-II proteases described herein, and/or comprises an amino acid sequence which is more than 60% homologous with that of at least one of the mature RP-II proteases shown in SEQ ID NO: 2, SEQ ID NO: 4, SEQ ID NO: 6, SEQ ID NO: 8, SEQ ID NO: 10, or SEQ ID NO: 12, such as more than 70%, 80% or even 90% homologous with said proteases, is encoded by a DNA sequence hybridizing with an oligonucleotide probe which also hybridizes with at least one of the DNA sequences encoding the RP-II proteases, the DNA and amino acid sequences of which are shown in SEQ ID NO 1, SEQ ID NO: 3, SEQ ID NO: 5, SEQ ID NO: 7, SEQ ID NO: 9, and SEQ ID NO: 11.

In the context of this application the term "homologue" or "homologous" is meant to comprise other parent (wild-type) RP-II proteases, which have a primary structure similar to that of another RP-II protease. The homology between two amino acid sequences is in this context described by the parameter "identity".

Sequence comparisons can be performed by standard methods, such as the Wilbur-Lipman method (Wilbur and Lipman, 1983, *Proceedings of the National Academy of Science USA* 80: 726–730), the Clustal method (Higgins, 1989, *CABIOS* 5: 151–153), or the GCG method Needleman, S. B. and Wunsch, C. D., (1970), Journal of Molecular Biology, 48, 443–453)

In order to determine the degree of identity between two RP-II proteases the GAP routine of the GCG package version 9.1 (Genetics Computer Group; 575 Science Drive, Madison, Wis., USA 53711) can be applied using the following parameters: gap creation penalty=8 and gap extension penalty=8 and all other parameters kept at their default values. The output from the routine is besides the calculation of the "Percent Identity" between the two sequences the amino acid alignment between the two sequences.

Based on this it is routine for a person skilled in the art to identify suitable homologous RP-II proteases and corresponding homologous positions, which can be modified according to the invention.

The term "parent" as used herein is typically a wild type protease, meaning that it has been described or found to be produced by a Bacillus species or strain isolated from natural sources. However, parent is also meant to comprise any protease, such as a variant protease, being used as starting material for further modifications to produce a further variant.

The term "variant" is intended to indicate a polypeptide which is derived from a RP-II protease as defined above and which has one or more of the properties i)–iii) which will be further discussed below. Typically, the variant differ from the RP-II protease by one or more amino acid residues, which, for instance, may have been added or deleted from either or both of the N-terminal or C-terminal end of the protease, inserted or deleted at one or more sites within the amino acid sequence of the protease, or substituted for one or more amino acid residues within, or at either or both ends of the amino acid sequence of the parent protease.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. The allelic variant of a polypeptide is a polypeptide encoded by an allelic variant of a gene.

The term "nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

NOMENCLATURE OE AMINO ACIDS

| A | = | Ala | = | Alanine |
|---|---|-----|---|---------|
| V | = | Val | = | Valine |
| L | = | Leu | = | Leucine |
| I | = | Ile | = | Isoleucine |
| P | = | Pro | = | Proline |
| F | = | Phe | = | Phenylalanine |
| W | = | Trp | = | Tryptophan |

-continued

| M | = | Met | = | Methionine |
|---|---|-----|---|------------|
| G | = | Gly | = | Glycine |
| S | = | Ser | = | Serine |
| T | = | Thr | = | Threonine |
| C | = | Cys | = | Cysteine |
| Y | = | Tyr | = | Tyrosine |
| N | = | Asn | = | Asparagine |
| Q | = | Gln | = | Glutamine |
| D | = | Asp | = | Aspartic Acid |
| E | = | Glu | = | Glutamic Acid |
| K | = | Lys | = | Lysine |
| R | = | Arg | = | Arginine |
| H | = | His | = | Histidine |
| X | = | Xaa | = | Any amino acid |

NOMENCLATURE OF NUCLEIC ACIDS

| A | = | Adenine | |
|---|---|---------|---|
| G | = | Guanine | |
| C | = | Cytosine | |
| T | = | Thymine | (only in DNA) |
| U | = | Uracil | (only in RNA) |
| N | = | A, C, G or T; | |
| R | = | A or G; | |
| Y | = | C or T; | |
| D | = | A, G or T; | |
| X | = | deoxyInosine. | |

Naming of RP-II Proteases

In describing the RP-II proteases of the invention the following abbreviations are used for ease of reference:
BLC=RP-II protease from *Bacillus licheniformis* (cf. U.S. Pat. No. 4,266,031),
AA513=RP-II protease from *Bacillus halmapalus* AA513
AC116=RP-II protease from *Bacillus licheniformis* AC116
BO32=RP-II protease from *Bacillus pumilus* BO32
CDJ31=RP-II protease from *Bacillus licheniformis* CDJ31
JA96=RP-II protease from *Bacillus pumilus* JA96
MPR=RP-II protease from *Bacillus subtilis* IS75 (cf. EP 369 817 B1)

Sequence Listing

In the appended Sequence Listing the RP-II proteases are indicated as:
SEQ. ID. NO. 1=BLC (DNA), SEQ. ID. NO. 2=BLC (AA),
SEQ. ID. NO. 3=AA513 (DNA), SEQ. ID. NO. 4=AA513 (AA),
SEQ. ID. NO. 5=AC116 (DNA), SEQ. ID. NO. 6=AC116 (AA)
SEQ. ID. NO. 7=BO32 (DNA), SEQ. ID. NO. 8=BO32 (AA)
SEQ. ID. NO. 9=CDJ31 (DNA), SEQ. ID. NO. 10=CDJ31 (AA)
SEQ. ID. NO. 11=JA96 (DNA), SEQ. ID. NO. 12=JA96 (AA)
SEQ. ID. NO. 13=BSMPR (DNA), SEQ. ID. NO. 14=BSMPR (AA)

Nomenclature and Conventions for Designation of Variants

In describing the various enzyme variants produced or contemplated according to the invention, the following nomenclatures and conventions have been adapted for ease of reference:

A frame of reference is first defined by aligning the amino acid sequence of a novel isolated or parent wild type enzyme with a suitable well known enzyme of the same group or class of enzymes. If nothing else is indicated herein, in the present instance the *Bacillus licheniformis* RP-II protease, first designated component C and therefore here abbreviated BLC, has been chosen as standard.

The alignment can be obtained by the GAP routine of the GCG package version 9.1 to number the variants using the following parameters: gap creation penalty=8 and gap extension penalty=8 and all other parameters kept at their default values.

By this a number of deletions and insertions will be defined in relation to the standard, here BLC. In the alignments deletions are indicated by asterixes (*) in the referenced sequence, and the referenced enzyme will be considered to have a gap at the position in question. Insertions are indicated by asterixes (*) in the sequence of the standard enzyme, and the positions in the referenced enzyme are given as the position number of the last amino acid residue where a corresponding amino acid residue exists in the standard enzyme with a lower case letter appended in alphabetical order, e.g. 82a, 82b, 82c, 82d, see FIG. 1

In case the referenced enzyme contains a N- or C-terminal extension in comparison to the standard enzyme, an N-terminal extension are given the position number 0a, 0b, etc.

A C-terminal extension will be given either the position number of the C-terminal amino acid residue of the standard enzyme with a lower case letter appended in alphabetical order, or simply a continued consecutive numbering.

The various modifications performed in a wild type enzyme is indicated in general using three elements as follows:
Original Amino Acid Position Substituted Amino Acid The notation E152G thus means a substitution of a glutamic acid in position 152 with a glycine.

In the case when the original amino acid residue may be any amino acid residue, a short hand notation may at times be used indicating only the position and substituted amino acid,
Position Substituted Amino Acid Such a notation is particular relevant in connection with modification(s) in homologous RP-II proteases.

Similarly when the identity of the substituting amino acid residue(s) is immaterial,
Original Amino Acid Position When both the original amino acid(s) and substituted amino acid(s) may comprise any amino acid, then only the position is indicated, e.g.: 152.

When the original amino acid(s) and/or substituted amino acid(s) may comprise more than one, but not all amino acid(s), then the selected amino acids are indicated inside brackets { },
Original Amino Acid Position {Substituted Amino Acid$_1$, . . . , Substituted Amino Acid$_n$}

For specific variants the specific three or one letter codes are used, including the codes Xaa and X to indicate any amino acid residue.
Substitutions The substitution of Alanine for Glutamic acid in position 152 is designated as:

Glu152Ala or E152A or the substitution of any amino acid residue acid for Glutamic acid in position 152 is designated as:

Glu152Xaa or E152X or

Glu152 or E152

The substitution of Glutamic acid for any amino acid residue in position 89 would thus be designated Xaa89Glu or X89E.

or

89Glu or 89E

Such a notation is particular relevant in connection with modification(s) in homologous RP-II proteases (vide infra).

89Glu is thus meant to comprise e.g. both a Arg89Glu modification in BLC and a Asn89Glu modification in JA96 (cf. FIG. 1b).

For a modification where the original amino acid(s) and/or substituted amino acid(s) may comprise more than one, but not all amino acid(s), the substitution of glycine, alanine, serine or threonine for arginine in position 152 would be indicated by Glu152{Gly,Ala,Ser,Thr} or E152{G,A,S,T} to indicate the variants

E152G, E152A, E152S, and E152T.

Deletions

A deletion of Glutamic acid in position 152 will be ndicated by:

Glu152* or E152*

Correspondingly the deletion of more than one amino acid residue, such as the deletion of glycine and leucine in positions 152 and 153 will be designated Glu152*+Thr153* or E152*+T153*

Insertions

The insertion of an additional amino acid residue such as e.g. a lysine after E152 is:

Glu152GluLys or E152EK; or when more than one amino acid residue is inserted, such as e.g. a Lys, Ala and Ser after E152 this is:

Glu152GluLysAlaSe (SEQ. ID NO:15) or E152EKAS

In such cases the inserted amino acid residue(s) are numbered by the addition of lower case letters to the position number of the amino acid residue preceding the inserted amino acid residue(s). In the above example the sequences 151 to 153 would thus be:

|  | 151 | 152 | 153 |  |  |
|---|---|---|---|---|---|
| Parent | S | - E | - T |  |  |
|  | 151 | 152 | 152a | 152b | 152c | 153 |
| Variant | S | - E | - K | - A | - S | - T (SEQ ID NO: 16) |

In cases where an amino acid residue identical to the existing amino acid residue is inserted it is clear that a degeneracy in the nomenclature arises. If for example a glutamic acid is inserted after the glutamic acid in the above example this would be indicated by E152EE. The same actual change could just as well be indicated as S151SE for the change from

|  | 151 | 152 | 153 |
|---|---|---|---|
| Parent to | S | - E | - T |
|  | 151 | 152 | 152a | 153 |
| Variant | S | - E | - E | -T (SEQ ID NO: 17) |
|  | 151 | 151a | 152 | 153 |

Such instances will be apparent to the skilled person, and the indication E152EE and corresponding indications for this type of insertions are thus meant to comprise such equivalent degenerate indications.

Correspondingly the modification of a residue and simultaneous insertion of a further residue may be designated in different ways as

V110PS=V110VS+V110P=V110P+P110PS indicating that the position 110 valine has been substituted by a proline and a serine.

Filling a Gap

Where a deletion in an enzyme exists in the reference comparison with the standard sequence used for the numbering, an insertion in such a position is indicated as:

*121Ser or *121S for the insertion of an serine in position 121

Multiple Modifications

Variants comprising multiple modifications are separated by pluses, e.g.:

Ser1Val+Glu152Ala or S1V+E152A representing modifications in positions 1 and 152 substituting serine and glutamic acid for valine and alanine, respectively. Or e.g. Arg8{Gly,Ala,Ser,Thr}+Glu152{Gly,Ala,Ser,Thr} designates the variants

| | | |
|---|---|---|
| Arg8Gly + Glu152Gly, | | Arg8Ala + Glu152Gly, |
| Arg8Ser + Glu152Gly, | | Arg8Thr + Glu152Gly, |
| Arg8Gly + Glu152Ala, | | Arg8Ala + Glu152Ala, |
| Arg8Ser + Glu152Ala, | | Arg8Thr + Glu152Ala, |
| Arg8Gly + Glu152Ser, | | Arg8Ala + Glu152Ser, |
| Arg8Ser + Glu152Ser, | | Arg8Thr + Glu152Ser, |
| Arg8Gly + Glu152Thr, | | Arg8Ala + Glu152Thr, |
| Arg8Ser + Glu152Thr, | and | Arg8Thr + Glu152Thr. |

This nomenclature is particularly relevant in relation to modifications aimed at substituting, replacing, inserting or deleting amino acid residues having specific common properties, such as residues of positive charge (K, R, H), negative charge (D, E), or conservative amino acid modification(s) of e.g. Arg8{Glu,Asp,Lys}+Glu152{Asp, Arg, Lys}, which signifies substituting a charged amino acid for another charged amino acid. See section "Detailed description of the invention" for further details.

Proteases

Enzymes cleaving the amide linkages in protein substrates are classified as proteases, or (interchangeably) peptidases (see Walsh, 1979, *Enzymatic Reaction Mechanisms.* W. H. Freeman and Company, San Francisco, Chapter 3).

Serine Proteases

A serine protease is an enzyme which catalyzes the hydrolysis of peptide bonds, and in which there is an essential serine residue at the active site (White, Handler and Smith, 1973 "*Principles of Biochemistry,*" Fifth Edition, McGraw-Hill Book Company, NY, pp. 271–272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease.

Description of the RP-II Protease from *B. licheniformis* ATCC 14580

For ease of reference, the following disclosure of recombinantly produced RP-II variants is based on the RP-II protease derived from the species *B. licheniformis* ATCC 14580, the amino acid sequence of which is shown in FIG. 1 below. It will be understood, however, that also functional analogues of RP-II proteases derivable from other Bacilli, such as the novel wild type RP-II proteases disclosed herein, may be modified in a manner similar to that described herein for the *B. licheniformis* ATCC 14580 RP-II protease. Accordingly, variants of such functional analogues are considered to be within the scope of the present invention. Examples of other Bacillus strains, which have been found to produce RP-II proteases, are *Bacillus pumilus, Bacillus subtilis,* and *Bacillus halmapalus.* However, it is expected that RP-II proteases will be found in many more Bacillus strains.

The parent *B. licheniformis* RP-II protease, BLC, as disclosed in U.S. Pat. No. 4,266,031 has the amino acid sequence shown in FIG. 1 and SEQ ID NO: 2, and the corresponding DNA sequence is shown in SEQ ID NO: 1.

DETAILED DESCRIPTION OF THE INVENTION

The invention will be disclosed in detail in the following sections.

Novel Isolated Rp-II Proteases and Nucleic Acid Sequences Encoding These

Accordingly, in a first embodiment the present invention relates to novel isolated RP-II proteases that are immunochemically identical or partially identical by cross-reaction with an antibody raised against or reactive with at least one epitope of a RP-II protease comprising the amino acid sequences of the mature peptides shown in the appended Sequence Listing ID No. 4, ID No. 6, ID No. 8, ID No. 10, or ID No. 12 (Jeg antager, at BLC og MPR er identiske med kendte sekvenser).

The immunological cross reactivity, may be assayed using an antibody raised against or reactive with at least one epitope of a RP-II protease comprising the amino acid sequence of the mature peptide shown in SEQ ID NO: 2, 4, 6, 8, 10, and 12. The antibody, which may either be monoclonal or polyclonal, may be produced by methods known in the art, e.g. as described by Hudson et al., 1989, Practical Immunology; 3. Ed. Blackwell Scientific Publications. The immunological cross-reactivity may be determined using assays known in the art, examples of which are Western Blotting or radial immunodiffusion assay, e.g. as described by Hudson et al., 1989. According to such assays the polypeptides of the invention can be characterized as being partially immunochemically identical, or preferably immunochemically identical to each other. The immunochemical properties can furthermore be determined immunologically by cross-reaction identity tests. The identity tests can be performed by the well-known Ouchterlony double immunodiffusion procedure or by tandem crossed immunoelectrophoresis according to N. H. Axelsen; Handbook of Immunoprecipitation-in-Gel Techniques; Blackwell Scientific Publications (1983), chapters 5 and 14. The terms "antigenic identity" and "partial antigenic identity" are described in the same book, chapters 5, 19 and 20.

In a second embodiment, the present invention relates to isolated RP-II proteases having an amino acid sequence which has a degree of identity to the mature polypeptides of SEQ ID NOs: 2, 4, 6, 8, 10 or 12 of at least about 60%, preferably at least about 70%, more preferably at least about 80%, even more preferably at least about 90%, most preferably at least about 95%, and even most preferably at least about 97%, which have protease activity (hereinafter "homologous RP-II proteases"). In a preferred embodiment, the homologous 20 RP-II proteases have an amino acid sequence which differs by five amino acids, preferably by four amino acids, more preferably by three amino acids, even more preferably by two amino acids, and most preferably by one amino acid from the amino acid sequence of the mature polypeptides of SEQ ID NO: 2, 4, 6, 8, 10 or 12. For purposes of the present invention, the degree of identity between two amino acid sequences is determined by the GAP method described above.

Preferably, RP-II proteases of the present invention comprise the amino acid sequence of SEQ ID NOs: 2, 4, 6, 8, 10, or 12 or allelic variants thereof; or a fragment thereof that has protease activity. In a more preferred embodiment, the RP-II proteases of the present invention comprise the amino acid sequence of SEQ ID NOs: 2, 4, 6, 8, 10 or 12. In another preferred embodiment, the RP-II proteases of the present invention comprise the amino acid sequences of the mature polypeptides of SEQ ID NO: 2, 4, 6, 8, 10, or 12, or allelic variants thereof; or a fragment thereof that has protease activity. In another preferred embodiment, the RP-II proteases of the present invention comprise the amino acid sequences of the mature polypeptides of SEQ ID NO: 2, 4, 6, 8, 10, or 12. In another preferred embodiment, the RP-II proteases of the present invention consist of the amino acid sequences of SEQ ID NO: 2, 4, 6, 8, 10, or 12 or an allelic variant thereof; or a fragment thereof, wherein the fragment has protease activity. In another preferred embodiment, the RP-II proteases of the present invention consists of the amino acid sequence of SEQ ID NOs: 2, 4, 6, 8, 10, or 12. In another preferred embodiment, RP-II proteases of the present invention consists of the amino acid sequences of the mature polypeptides of SEQ ID NO: 2, 4, 6, 8, 10, or 12, or an allelic variant thereof; or a fragment thereof that has protease activity. In another preferred embodiment, the RP-II proteases of the present invention consist of the amino acid sequences of the mature polypeptides of SEQ ID NO: 2, 4, 6, 8, 10, or 12.

In a third embodiment, the present invention relates to isolated RP-II proteases encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) a nucleic acid sequence encoding a RP-II protease of SEQ ID NO: 2, 4, 6, 8, 10, 12, or 14, (ii) the cDNA sequence encoding a RP-II protease of SEQ ID NO:2, 4, 6, 8, 10, 12, or 14, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO:2, 4, 6, 8, 10, 12, or 14 may be at least 100 nucleotides or preferably at least 200 nucleotides. Moreover, the subsequence may encode a RP-II protease fragment which has protease activity.

In a fourth embodiment, the present invention relates to isolated RP-II proteases encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) the nucleic acid sequence of SEQ ID NO:1, 3, 5, 7, 9, 11, or 13, (ii) the cDNA sequence of SEQ ID NO:1, 3, 5, 7, 9, 11, 13 (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO:1, 3, 5, 7, 9, 11, or 13 may be at least 100 nucleotides or preferably at least 200 nucleotides. Moreover, the subsequence may encode a polypeptide fragment which has protease activity.

The nucleic acid sequence of SEQ ID NO:1, 3, 5, 7, 9, 11, or 13 or a subsequence thereof, as well as the amino acid sequence of SEQ ID NO:2, 4, 6, 8, 10 12, or 14 or a fragment thereof, may be used to design a nucleic acid probe to identify and clone DNA encoding RP-II proteases from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a RP-II protease. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1, 3, 5, 7, 9, 11, or 13, or a subsequence thereof, the carrier material is used in a Southern blot. For purposes of the present invention, hybridization indicates that the nucleic acid sequence hybridizes to a nucleic acid probe corresponding to the nucleic acid sequence shown in SEQ ID NO:1, 3, 5, 7, 9, 11, or 13, its complementary strand, or a subsequence thereof, under very low to very high stringency conditions. Molecules to which the nucleic acid probe hybridizes under these conditions are detected using X-ray film.

For long probes of at least 100 nucleotides in length, very low to very high stringency conditions are defined as prehybridization and hybridization at 42° C. in 6×SSC, 5×Denhardt's solution, 0.2% SDS, 100 mg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes or synthetic oligonucleotides probes which are about 15 nucleotides to about 30 nucleotides in length, stringency conditions are defined as prehybridization, hybridization, and washing post-hybridization at 5° C. to 10° C. below the calculated Tm using the calculation according to Bolton and McCarthy (1962, Proceedings of the National Academy of Sciences USA 48:1390) in 6×SSC, 5×Denhardt's solution, 0.05% sodium pyrophosphate, 100 mg/ml sheared and denatured herring sperm DNA, 0.5% SDS following standard Southern blotting procedures.

For short end-labeled 32P probes or synthetic oligonucleotides end-labeled 32P probes which are about 15 nucleotides to about 30 nucleotides in length, the carrier material is washed in prewarmed 6×SCC plus 0.05% sodium pyrophosphate for 15 to 30 minutes at 5° C. to 10° C. below the calculated Tm. The wash is repeated until a Geiger counter is not exhibiting above background radioactivity.

In a further embodiment, the present invention relates to isolated nucleic acid sequences encoding RP-II proteases having an amino acid sequence which has a degree of identity to the mature peptides of SEQ ID NOs:2, 4, 6, 8, 10 or 12 of at least about 60%, preferably at least about 70%, more preferably at least about 80%, even more preferably at least about 90%, most preferably at least about 95%, and even most preferably at least about 97%, which have protease activity (hereinafter "homologous RP-II proteases"). In a preferred embodiment, the homologous RP-II proteases have an amino acid sequence which differs by five amino acids, preferably by four amino acids, more preferably by three amino acids, even more preferably by two amino acids, and most preferably by one amino acid from the amino acid sequence of the mature polypeptides of SEQ ID NO:2, 4, 6, 8, 10 or 12. For purposes of the present invention, the degree of identity between two amino acid sequences is determined by the GAP method described above.

Preferably, the nucleic acid sequences of the present invention encode RP-II proteases that comprise the amino acid sequence of SEQ ID NOs: 2, 4, 6, 8, 10, or 12 or allelic variants thereof; or a fragment thereof that has protease activity. In a more preferred embodiment, the nucleic acid sequence of the present invention encodes a RP-II protease that comprises the amino acid sequence of SEQ ID NOs:2, 4, 6, 8, 10 or 12. In another preferred embodiment, the nucleic acid sequence of the present invention encodes a RP-II protease that comprises an amino acid sequence of the mature polypeptides of SEQ ID NO:2, 4, 6, 8, 10, or 12, or allelic variants thereof; or a fragment thereof that has protease activity. In another preferred embodiment, the nucleic acid sequence of the present invention encodes a RP-II protease that comprises the amino acid sequence of a mature polypeptide of SEQ ID NO: 2, 4, 6, 8, 10, or 12. In another preferred embodiment, the nucleic acid sequence of the present invention encodes a RP-II protease that consists of the amino acid sequence of SEQ ID NO: 2, 4, 6, 8, 10, or 12, or an allelic variant thereof; or a fragment thereof, wherein the polypeptide fragment has protease activity. In another preferred embodiment, the nucleic acid sequence of the present invention encodes a RP-II protease that consists of the amino acid sequence of SEQ ID NO: 2, 4, 6, 8, 10, or 12. In another preferred embodiment, the nucleic acid sequence of the present invention encodes a RP-II protease that consists of the amino acid sequence of a mature polypeptide of SEQ ID NO: 2, 4, 6, 8, 10, or 12, or an allelic variant thereof; or a fragment thereof that has protease activity. In another preferred embodiment, the nucleic acid sequence of the present invention encodes a RP-II protease that consists of amino acid sequence of a mature polypeptide of SEQ ID NO: 2, 4, 6, 8, 10, or 12.

The present invention also encompasses nucleic acid sequences which encode a RP-II protease having the amino acid sequence of SEQ ID NO: 2, 4, 6, 8, 10, or 12, which differ from SEQ ID NO: by virtue of the degeneracy of the genetic code. The present invention also relates to subsequences of SEQ ID NO: 1, 3, 5, 7, 9, or 11 which encode fragments of SEQ ID NO: 2, 4, 6, 8, 10, or 12 which have protease activity.

A subsequence of SEQ ID NO: 1, 3, 5, 7, 9, or 11 is a nucleic acid sequence encompassed by SEQ ID NO:1, 3, 5, 7, 9, or 11 except that one or more nucleotides from the 5' and/or 3' end have been deleted.

In a yet further embodiment, the present invention relates to isolated nucleic acid sequences encoding RP-II proteases of the invention which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) the nucleic acid sequence of SEQ ID NO: 1, 3, 5, 7, 9, or 11, (ii) the cDNA sequence of SEQ ID NO:1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO: 1, 3, 5, 7, 9, or 11 may be at least 100 nucleotides or preferably at least 200 nucleotides. Moreover, the subsequence may encode a polypeptide fragment which has protease activity.

The polypeptides encoded by the isolated nucleic acid sequences of the present invention have at least 20%, preferably at least 40%, more preferably at least 60%, even more preferably at least 80%, even more preferably at least 90%, and most preferably at least 100% of the protease activity of the mature RP-II proteases of SEQ ID NO: 2, 4, 6, 8, 10, or 12.

Description of RP-II Protease Variants of the Invention

In the following specific classes of RP-II protease variants of the invention having improved properties are described as well as the concepts used for the design of such variants.

Stabilization by Modification of Asn-Gly Pairs

It is known that at alkaline pH, the side chain of Asn may interact with the NH group of a sequential neighbouring amino acid to form an isoAsp residue where the backbone goes through the Asp side chain. This will leave the backbone more vulnerable to proteolysis. The deamidation is much more likely to occur if the residue that follows is a Gly. Changing the Asn in front of the Gly or the Gly will prevent this from happening and thus improve the stability, especially as concerns thermo- and storage stability.

The invention consequently further relates to a RP-II protease variant, in which either or both residues of any of the Asn-Gly sequence appearing in the amino acid sequence of the parent RP-II protease is/are deleted or substituted with a residue of a different amino acid.

The Asn and/or Gly residue may, for instance, be substituted with a residue of an amino acid selected from the group consisting of A, Q, S, P, T and Y.

More specifically, any of the Asn or Gly residues of the Asn-Gly occupying positions 68–69, 182–183 and/or 192–193 of the BLC protease; positions 68–69, and/or 192–193 of the AC116 protease, positions 68–69 and/or 192–193 of the CDJ-31 protease, positions 45–46, 74–75, 187–188, and/or 191–192 of the BO32 protease, positions 45–46, 74–75, 187–188 and/or 191–192 of the JA96 protease, and positions 90–91, and/or 195–196 of the AA513 protease, and positions 78–79, 103–104 and or 192a–192b of the MPR protease may be deleted or substituted with a residue of an amino acid selected from the group consisting of A, Q, S, P, T and Y.

Specific variants of BLC are:
N68{A,Q,S,P,T,Y}; G69{A,Q,S,P,T,Y}
N68{A,Q,S,P,T,Y}+G69{A,Q,S,P,T,Y}
N182{A,Q,S,P,T,Y}; G183{A,Q,S,P,T,Y}
N182{A,Q,S,P,T,Y}+G183{A,Q,S,P,T,Y}
N192{A,Q,S,P,T,Y}; G193{A,Q,S,P,T,Y}
N192{A,Q,S,P,T,Y}+G193{A,Q,S,P,T,Y}
N68{A,Q,S,P,T,Y}+N182{A,Q,S,P,T,Y}
N68{A,Q,S,P,T,Y}+N182{A,Q,S,P,T,Y}+N192{A,Q,S,P,T,Y}

Specific variants of the AC116 protease are:
N68{A,Q,S,P,T,Y}; G69{A,Q,S,P,T,Y}
N68{A,Q,S,P,T,Y}+G69{A,Q,S,P,T,Y}
N192{A,Q,S,P,T,Y}; G193{A,Q,S,P,T,Y}
N192{A,Q,S,P,T,Y}+G193{A,Q,S,P,T,Y}
N68{A,Q,S,P,T,Y}+N192{A,Q,S,P,T,Y}

Specific variants of CDJ-31 are:
N68{A,Q,S,P,T,Y}; G69{A,Q,S,P,T,Y}
N68{A,Q,S,P,T,Y}+G69{A,Q,S,P,T,Y}
N192{A,Q,S,P,T,Y}; G193{A,Q,S,P,T,Y}
N192{A,Q,S,P,T,Y}+G193{A,Q,S,P,T,Y}
N68{A,Q,S,P,T,Y}+N192{A,Q,S,P,T,Y}

Specific variants of B032 are:
N45{A,Q,S,P,T,Y}; G46{A,Q,S,P,T,Y}
N45{A,Q,S,P,T,Y}+G46{A,Q,S,P,T,Y}
N74{A,Q,S,P,T,Y}; G75{A,Q,S,P,T,Y}
N74{A,Q,S,P,T,Y}+G75{A,Q,S,P,T,Y}
N187{A,Q,S,P,T,Y}; G188{A,Q,S,P,T,Y}
N187{A,Q,S,P,T,Y}+G188{A,Q,S,P,T,Y}
N192{A,Q,S,P,T,Y}; G193{A,Q,S,P,T,Y}
N192{A,Q,S,P,T,Y}+G193{A,Q,S,P,T,Y}
N45{A,Q,S,P,T,Y}+N74{A,Q,S,P,T,Y}
N45{A,Q,S,P,T,Y}+N187{A,Q,S,P,T,Y}
N45{A,Q,S,P,T,Y}+N192{A,Q,S,P,T,Y}
N74{A,Q,S,P,T,Y}+N187{A,Q,S,P,T,Y}
N74{A,Q,S,P,T,Y}+N192{A,Q,S,P,T,Y}
N187{A,Q,S,P,T,Y}+N192{A,Q,S,P,T,Y}
N45{A,Q,S,P,T,Y}+N74{A,Q,S,P,T,Y}+N187{A,Q,S,P,T,Y}
N45{A,Q,S,P,T,Y}+N74{A,Q,S,P,T,Y}+N192{A,Q,S,P,T,Y}
N45{A,Q,S,P,T,Y}+N187{A,Q,S,P,T,Y}+N192{A,Q,S,P,T,Y}
N74{A,Q,S,P,T,Y}+N187{A,Q,S,P,T,Y}+N192{A,Q,S,P,T,Y}
N45{A,Q,S,P,T,Y}+N74{A,Q,S,P,T,Y}+N187{A,Q,S,P,T,Y}+N192{A,Q,S,P,T,Y}

Specific variants of JA96 are:
N45{A,Q,S,P,T,Y}; G46{A,Q,S,P,T,Y}
N45{A,Q,S,P,T,Y}+G46{A,Q,S,P,T,Y}
N74{A,Q,S,P,T,Y}; G75{A,Q,S,P,T,Y}
N74{A,Q,S,P,T,Y}+G75{A,Q,S,P,T,Y}
N187{A,Q,S,P,T,Y}; G188{A,Q,S,P,T,Y}
N187{A,Q,S,P,T,Y}+G188{A,Q,S,P,T,Y}
N192{A,Q,S,P,T,Y}; G193{A,Q,S,P,T,Y}
N192{A,Q,S,P,T,Y}+G193{A,Q,S,P,T,Y}
N45{A,Q,S,P,T,Y}+N74{A,Q,S,P,T,Y}
N45{A,Q,S,P,T,Y}+N187{A,Q,S,P,T,Y}
N45{A,Q,S,P,T,Y}+N192{A,Q,S,P,T,Y}
N74{A,Q,S,P,T,Y}+N187{A,Q,S,P,T,Y}
N74{A,Q,S,P,T,Y}+N192{A,Q,S,P,T,Y}
N187{A,Q,S,P,T,Y}+N192{A,Q,S,P,T,Y}
N451{A,Q,S,P,T,Y}+N74{A,Q,S,P,T,Y}+N187{A,Q,S,P,T,Y}
N45{A,Q,S,P,T,Y}+N74{A,Q,S,P,T,Y}+N192{A,Q,S,P,T,Y}
N45{A,Q,S,P,T,Y}+N187{A,Q,S,P,T,Y}+N192{A,Q,S,P,T,Y}
N74{A,Q,S,P,T,Y}+N187{A,Q,S,P,T,Y}+N192{A,Q,S,P,T,Y}
N45{A,Q,S,P,T,Y}+N74{A,Q,S,P,T,Y}+N187{A,Q,S,P,T,Y}+N192{A,Q,S,P,T,Y}

Specific variants of AA513 are:
N90{A,Q,S,P,T,Y}; G91{A,Q,S,P,T,Y}
N90{A,Q,S,P,T,Y}+G91{A,Q,S,P,T,Y}
N195{A,Q,S,P,T,Y}; G196{A,Q,S,P,T,Y}
N195{A,Q,S,P,T,Y}+G196{A,Q,S,P,T,Y}
N90{A,Q,S,P,T,Y}+N195{A,Q,S,P,T,Y}

Specific variants of MPR are:
N78{A,Q,S,P,T,Y}; G79{A,Q,S,P,T,Y}
N78{A,Q,S,P,T,Y}+G79{A,Q,S,P,T,Y}
N103{A,Q,S,P,T,Y}; G104{A,Q,S,P,T,Y}
N103{A,Q,S,P,T,Y}+G104{A,Q,S,P,T,Y}
N192a{A,Q,S,P,T,Y}; G192b{A,Q,S,P,T,Y}
N192a{A,Q,S,P,T,Y}+G192b{A,Q,S,P,T,Y}
N78{A,Q,S,P,T,Y}+N103{A,Q,S,P,T,Y}
N78{A,Q,S,P,T,Y}+N192a7{A,Q,S,P,T,Y}
N103{A,Q,S,P,T,Y}+N192a{A,Q,S,P,T,Y}
N78{A,Q,S,P,T,Y}+N103{A,Q,S,P,T,Y}+N192a{A,Q,S,P,T,Y}

Removal of Autoproteolysis Sites

According to a further aspect of the invention autoproteolysis sites may be removed by changing the amino acids at a autoproteolysis site. Since the RP-II proteases cleaves at Glu and Asp residues it is preferred to modify such residues of a parent RP-II protease having the same or a similar specificity, preferably by substituting with any other amino acid except Glu.

Since the parent RP-II proteases is specific mostly towards Glu and to a minor extend towards Asp residues, the modification of this parent (trypsin-like) RP-II protease may preferably be made by changing Glu to another amino acid residue (including Asp). Experiments have indicated that the substitution of Ala for Glu or Asp provides good results.

The following Glu and Asp residue positions are found in the BLC protease: E101, E104, E152, E173, E209, D6, D7, D51, D135, D161, D212.

Specific BLC variants are thus E101A, E104A, E152A, E173A, E209A, D6A, D7A, D51A, D135A, D161A, D212A, and double, triple, quadruple, etc. combinations thereof.

In JA96 Glu and Asp are found in positions: E81, E143, E151, E202, D5, D6, D69, D96, D103, D135, D152, D161, D173.

Specific JA96 variants are thus E81A, E143A, E151A, E202A, D5A, D6A, D69A, D96A, D103A, D135A, D152A, D161A, D173A, and double, triple, quadruple, etc. combinations thereof.

Corresponding variants are easily identified in any other RP-II protease.

Alternatively autoproteolysis can be prevented by changing the amino acid residue occupying the $1^{st}$ and/or $2^{nd}$ position following the Glu or Asp residue in question to Pro. For instance, this may in BLC be done in the positions 174 and/or 175 as follows:
Q174P
S175P
Q174P+S175P or in a similar manner in JA96 in positions 152 and/or 153 as D152P; T153P; or D152P+T153P Corresponding variants are easily identified in any other RP-II protease.

Removal of Critical Oxidation Sites

In order to increase the stability of the RP-II protease it may be advantageous to substitute critical oxidation sites, such as methionines, with other amino acid residues which are not subject to oxidation.

Accordingly, in a further embodiment the present invention relates to a RP-II protease variant, in which one or more amino acid residues susceptible to oxidation, especially methionine residues exposed to the surface of the molecule, is/are deleted or replaced with another amino acid residue less susceptible to oxidation. The amino acid residue less susceptible to oxidation may for instance be selected from the group consisting of A, E, N, Q, I, L, S and K.

Specific such variants comprises at least one of the substitutions M36S,A,N,Q,K; M160S,A,N,Q,K
of the BLC protease,
M144S,A, N, Q, K
of the AC116 and CDJ31 proteases,
M67S,A,N,Q,K; M79S,A,N,Q,K; M137S,A,N,Q,K; M144S,A,N,Q,K; M171S,A,N,Q,K;
of the BO32 and JA96 proteases,
M159S,A,N,Q,K;
of the BO32 protease.

Modification of Tryptophan Residues

In order to stabilize the protein it may be advantageous to replace or delete tryptophan residues at the surface of the protein, e.g. as described in U.S. Pat. No. 5,118,623. The tryptophan residues may advantageously be substituted for F, T, Q or G. Thus, in a further embodiment the invention relates to a RP-II variant comprising one or more of the following substitutions:

BLC:
   W35{F,T,Q,G}
   W88{F,T,Q,G}
   W142{F,T,Q,G}
   W217{F,T,Q,G}

AC116:
   W35{F,T,Q,G}
   W88{F,T,Q,G}
   W142{F,T,Q,G}
   W217{F,T,Q,G}

CDJ31:
   W142{F,T,Q,G}
   W217{F,T,Q,G}

B032:
   W142{F,T,Q,G}

JA96:
   W142{F,T,Q,G}

AA513:
   W30{F,T,Q,G}
   W72{F,T,Q,G}
   W142{F,T,Q,G}

MPR:
   W57{F,T,Q,G}
   W88{F,T,Q,G}
   W112{F,T,Q,G}
   W142{F,T,Q,G}
   W217{F,T,Q,G}

Variants with Improved Wash Performance

The ability of an enzyme to catalyse the degradation of various naturally occurring substrates present on the objects to be cleaned during e.g. wash is often referred to as its washing ability, washability, detergency, or wash performance. The present invention provides novel RP-II proteases for the use in detergents and novel RP-II protease variants exhibiting an improved wash performance as compared to that of the parent RP-II protease.

Examples of specific BLC variants comprises one or more of the following substitutions:
E152A,R,K,G
E173A
E209A
E152G+G164R In relation to wash performance it has been found that the modification of certain tyrosine residues to phenylalanine provides an improved wash performance. Without being bound by any specific theory, it is believed that titration of these Tyr residues in the alkaline wash liquor has negative effects that are alleviated by replacing the Tyr residues with other residues, especially Phe or Trp, particularly Phe.

In the BLC parent RP-II protease, the following tyrosine residues may be modified:
17, 19, 50, 72, 74, 82, 95, 97, 112, 115, 117, 132, 154, 158, 163, 195, 200

Examples of specific BLC variants comprises one or more of the following substitutions:
Y17F,W
Y19F,W
Y50F,W
Y72F,W
Y74F,W
Y82F,W
Y95F,W
Y97F,W
Y112F,W
Y115F,W
Y117F,W
Y132F,W
Y154F,W
Y158F,W
Y163F,W
Y195F,W
Y200F,W In the AC116 parent RP-II protease, the following tyrosine residues may be modified:
19, 50, 72, 74, 82, 95, 97, 112, 115, 117, 132, 154, 163, 172, 195, 200

Examples of specific AC116 variants comprises one or more of the following substitutions:
Y19F,W
Y50F,W
Y72F,W
Y74F,W
Y82F,W
Y95F,W
Y97F,W
Y112F,W
Y115F,W
Y117F,W
Y132F,W
Y154F,W
Y158F,W
Y163F,W
Y172F,W
Y195F,W
Y200F,W In the CDJ31 parent RP-II protease, the following tyrosine residues may be modified:
17, 19, 50, 72, 74, 82, 88, 95, 97, 112, 115, 117, 132, 154, 158, 163, 172, 195, 200

Examples of specific CDJ31 variants comprises one or more of the following substitutions:
Y17F,W
Y19F,W
Y50F,W
Y72F,W
Y74F,W
Y82F,W
Y88F,W
Y95F,W
Y97F,W
Y112F,W

Y115F,W
Y117F,W
Y132F,W
Y154F,W
Y158F,W
Y163F,W
Y172F,W
Y195F,W
Y200F,W

In the BO32 parent RP-II protease, the following tyrosine residues may be modified:
19, 50, 57, 64, 83, 88, 95, 112, 132, 157, 158, 185, 206

Examples of specific BO32 variants comprises one or more of the following substitutions:
Y19F,W
Y50F,W
Y57F,W
Y64F,W
Y83F,W
Y88F,W
Y95F,W
Y112F,W
Y132F,W
Y157F,W
Y158F,W
Y185F,W
Y206F,W In the JA96 parent RP-II protease, the following tyrosine residues may be modified:
19, 24, 50, 57, 64, 83, 88, 95, 112, 132, 157, 158, 186, 206

Examples of specific JA96 variants comprises one or more of the following substitutions:
Y19F,W
Y24F,W
Y50F,W
Y57F,W
Y64F,W
Y83F,W
Y88F,W
Y95F,W
Y112F,W
Y132F,W
Y157F,W
Y158F,W
Y186F,W
Y206F,W In the AA513 parent RP-II protease, the following tyrosine residues may be modified:
24, 74, 77, 84, 88, 97, 130, 132, 167, 172, 186

Examples of specific AA513 variants comprises one or more of the following substitutions:
Y24F,W
Y74F,W
Y77F,W
Y84F,W
Y88F,W
Y87F,W
Y97F,W
Y130F,W
Y132F,W
Y167F,W
Y172F,W
Y186F,W In the MPR parent RP-II protease, the following tyrosine residues may be modified:
19, 26d, 30, 50, 72, 74, 77, 82, 95, 97, 113, 115, 154, 158, 163, 172, 175, 200, 216

Examples of specific MPR variants comprises one or more of the following substitutions:
Y19F,W
Y26dF,W
Y30F,W
Y50F,W
Y72F,W
Y74F,W
Y77F,W
Y82F,W
Y95F,W
Y97F,W
Y113F,W
Y115F,W
Y154F,W
Y158F,W
Y163F,W
Y172F,W
Y175F,W
Y200F,W
Y216F,W Variants with Raised/lowered pI The concept is to alter the pI for the protein such that it approaches the pH of the detergent formulation. The pI can be raised by changing negatively charged or neutral amino acids to positively charged amino acids or by changing positively charged residues to more positively charged residues. The pI can be lowered by changing positively charged or neutral amino acids to negatively charged amino acids or by changing negatively charged amino acids to more negatively charged amino acids.

Accordingly, in accordance with this embodiment the invention relates to a RP-II protease variant, in which the net electrostatic charge of the parent RP-II protease has been changed by deleting or substituting one or more negatively charged amino acid residues by neutral or positively charged amino acid residue(s), and/or by substituting one or more neutral amino acid residues by positively or negatively charged amino acid residue(s), and/or by deleting or substituting one or more positively charged amino acid residue(s) by neutral or negatively charged amino acid residue(s), thereby obtaining variant which either has a lower or higher pI as compared to the pI of its parent protease.

In order to have any effect on the pI, the positions suited for substitution should be located so as to be at least partially exposed on the protein surface. It is preferred that the amino acid substitutions result in a variant protease having a pI just below the pH of the detergent.

In particular, an amino acid residue located in one or more positions of the parent RP-II protease and exposed at the surface of the molecule may be substituted:

It should be noted that, according to the invention, any one of the modifications of the amino acid sequence indicated above for the RP-II protease variants may be combined with any one of the other modifications mentioned above, where appropriate.

Methods of Preparing RP-II Proteases and Variants

The novel RP-II proteases of the invention may be produced by conventional methods by fermentation of the microorganisms from which they were isolated in suitable media with subsequent purification from the fermentation broth.

However, it is preferred to use the isolated DNA sequences of the invention for the production of both the novel isolated RP-II proteases and the variants thereof. Such methods are described in detail below.

Specifically for the variants, several methods for introducing mutations into genes are known in the art. After a brief discussion of cloning RP-II protease-encoding DNA sequences (which for instance encode functional analogous of the RP-II proteases of the invention), methods for generating mutations at specific sites within the RP-II protease encoding sequence will be indicated. The mutated polynucleotide sequences are subsequently used for the production of the RP-II protease variants of the invention in a manner similar to that for producing the novel isolated RP-II proteases.

Cloning a DNA Sequence Encoding a RP-II Protease

The DNA sequence encoding a parent RP-II protease may be isolated from any cell or microorganism producing the RP-II protease in question by various methods, well known in the art. Useful sources producing RP-II proteases are gram-positive bacteria belonging to the genus Bacillus, such as *Bacillus licheniformis, Bacillus pumilus, Bacillus halmapalus, Bacillus alkalophilus, Bacillus amyloliquefaciens, Bacillus brevis, Bacillus circulans, Bacillus coagulans, Bacillus lautus, Bacillus lentus, Bacillus megaterium, Bacillus stearothermophilus, Bacillus subtilis,* or *Bacillus thuringiensis.*

In another preferred embodiment, the nucleic acid sequences are obtained from a *Bacillus licheniformis, Bacillus pumilus,* or *Bacillus halmapalus.*

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

In another more preferred embodiment, the nucleic acid sequence is the sequence contained in plasmid pUC19/AC116, pUC/CDJ31, pUC/BO32, pUC/JA96, or pUC/AA513, which is contained in DSM 12841: *E. coli* pUC19/AC116, DSM 12842: *E. coli* pUC/CDJ31, DSM 12843: *E. coli* pUC/BO32, DSM 12844: *E. coli* pUC/JA96, and DSM 12845: *E. coli* pUC/AA513, respectively. In another preferred embodiment, the nucleic acid sequence is that of SEQ ID NO: 1, 3, 5, 7, 9, or 11, which encodes a mature polypeptide.

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Bacillus, or another or related organism and thus, for example, may be an allelic or species variant of the polypeptide encoding region of the nucleic acid sequence.

More specifically, first a genomic DNA and/or cDNA library may be constructed using chromosomal DNA or messenger RNA from the organism that produces the RP-II protease to be studied. Then, if the amino acid sequence of the RP-II protease is known, homologous, labelled oligonucleotide probes may be synthesized and used to identify RP-II protease-encoding clones from a genomic library prepared from the organism in question. Alternatively, a labelled oligonucleotide probe containing sequences homologous to a known RP-II protease could be used as a probe to identify RP-II protease encoding clones, using hybridization and washing conditions of lower stringency.

Yet another method for identifying RP-II protease producing clones would involve inserting fragments of genomic DNA into an expression vector, such as a plasmid, transforming RP-II protease-negative bacteria with the resulting genomic DNA library, and then plating the transformed bacteria onto agar containing a substrate for the RP-II protease thereby allowing clones expressing the RP-II protease to be identified.

Alternatively, the DNA sequence encoding the enzyme may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *The EMBO J.* 3, 1984, pp. 801–805. According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence, in accordance with standard techniques. The DNA sequence may also be prepared by polymerase chain reaction (PCR) using specific or degenerate primers, for instance as described in U.S. Pat. No. 4,683,202 or R. K. Saiki et al., *Science* 239, 1988, pp. 487–491.

Mutant Nucleic Acid Sequences and Methods for the Production Thereof

The present invention also relates to mutant nucleic acid sequences comprising at least one mutation in the mature polypeptide coding sequence of a functional RP-II protease analogue, and especially of SEQ ID NO:1, 3, 5, 7, 9, 11, or 13. wherein the mutant nucleic acid sequence encodes a functional analogue of a RP-II protease that may be modified in comparison to the parent protease depending on the nature of the mutation performed, especially variants of the mature polypeptide of SEQ ID NO:2, 4, 6, 8, 10, 12 or 14, or a fragment thereof which has protease activity.

Modification of a nucleic acid sequence of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

The present invention further relates to methods for producing a mutant nucleic acid sequence, comprising introducing at least one mutation into the mature polypeptide coding sequence of a functional RP-II protease analogue, and especially of SEQ ID NO:1, 3, 5, 7, 9, 11, or 13, wherein the mutant nucleic acid sequence encodes a functional analogue of a RP-II protease that may be modified in comparison to the parent protease depending on the nature of the mutation performed, especially variants of the mature polypeptide of SEQ ID NO:2, 4, 6, 8, 10, 12 or 14, or a fragment thereof which has protease activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Once a RP-II protease encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the RP-II protease encoding sequence, is created in a vector carrying the RP-II protease gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984, Biotechnology 2:646–639). U.S. Pat. No. 4,760,025, by Estell et al., issued Jul. 26, 1988, discloses the introduction of oligonucleotides encoding multiple mutations by performing minor alterations of the cassette, however, an even greater variety of mutations can be introduced at any one time by the Morinaga method, because a multitude of oligonucleotides, of various lengths, can be introduced.

Another method of introducing mutations into RP-II protease encoding sequences is described in Nelson and Long, *Analytical Biochemistry* 180, 1989, pp. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Expression of RP-II Proteases and Variants Thereof

According to the invention, a novel isolated polynucleotide or a a modified polynucleotide sequence encoding a RP-II protease or a variant thereof produced by methods described above, or any alternative methods known in the art, can be expressed, in enzyme form, using a DNA construct or an expression vector which typically includes control sequences encoding a promoter, operator, ribosome binding site, translation initiation signal, and, optionally, a repressor gene or various activator genes.

While intracellular expression may be advantageous in some respects, e.g. when using certain bacteria as host cells, it is generally preferred that the expression is extracellular. As mentioned above the RP-II proteases of the invention comprising the amino acid sequence shown in the SEQ ID NO: 1, 4, 6, 8, 10, or 12 comprise a pre-region consisting of a signal peptide and a pro-peptide permitting secretion of the expressed protease into the culture medium. If desirable, this pre-region may be substituted with a different pre-region or signal sequence, convenient accomplished by substitution of the DNA sequences encoding the respective pre-regions.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

An isolated nucleic acid sequence encoding a RP-II protease of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a RP-II protease of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention to produce the RP-II proteases of the invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell to produce the RP-II proteases of the invention are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (Cyc1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

In a preferred embodiment, the signal peptide coding region is indicated in SEQ ID NO:1, 3, 5, 7, 9, 11, and 13, e.g. for BLC nucleotides 1 to 93 of of SEQ ID NO:1, which encodes the corresponding amino acids of SEQ ID NO:2 4, 6, 8, 10, 12 and 14, e.g. for BLC amino acids −94 to −64 of of SEQ ID NO:2.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant olypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

In a preferred embodiment, the propeptide coding region is indicated in SEQ ID NO:1, 3, 5, 7, 9, 11, and 13, e.g. for BLC nucleotides 94 to 282 of SEQ ID NO:1 which encodes the corresponding amino acids of SEQ ID NO:2 4, 6, 8, 10, 12 and 14, e.g. for BLC amino acids −63 to −1 of SEQ ID NO:2.

Where both signal peptide and propeptide regions are present at the amino terminus of a polypeptide, the propeptide region is positioned next to the amino terminus of the polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the olypeptide would be operably linked with the regulatory sequence.

It is often suitable to provide the various control or regulatory sequences from the same source.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, a bacteriophage, or an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the RP-II proteases of the invention. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, such as a bacterial or a fungal (including yeast) cell, or a non-unicellular microorganism, e.g., a eukaryote, such as a mammal, an insect, or a plant.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus pumilus, Bacillus halmapalus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium* Series No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal patent cell is a

*Fusarium venenatum* (Nirenberg sp. nov.) cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophila* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

The present invention therefore also relates to a transgenic plant, plant part or plant cell which has been transformed with a DNA sequence encoding the proteases or variants of the invention so as to express and produce this enzyme in recoverable quantities. The enzyme may be recovered from the plant or plant part.

The transgenic plant can be dicotyledonous or monocotyledonous, for short a dicot or a monocot. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism *Arabidopsis thaliana*.

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the enzyme of the invention may be constructed in accordance with methods known in the art. In short the plant or plant cell is constructed by incorporating one or more expression constructs encoding the enzyme of the invention into the plant host genome and propagating the resulting modified plant or plant cell into a transgenic plant or plant cell.

Conveniently, the expression construct is a DNA construct which comprises a gene encoding the enzyme of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, eg on the basis of when, where and how the enzyme is desired to be expressed. For instance, the expression of the gene encoding the enzyme of the invention may be constitutive or inducible, or may be developmental, stage or tissue specific, and the gene product may be targeted to a specific tissue or plant part such as seeds or leaves. Regulatory sequences are eg described by Tague et al, Plant, Phys., 86, 506, 1988.

For constitutive expression the 35S-CaMV promoter may be used (Franck et al., 1980. Cell 21: 285–294). Organ-specific promoters may eg be a promoter from storage sink tissues such as seeds, potato tubers, and fruits (Edwards & Coruzzi, 1990. Annu. Rev. Genet. 24: 275–303), or from metabolic sink tissues such as meristems (Ito et al., 1994. Plant Mol. Biol. 24: 863–878), a seed specific promoter such as the glutelin, prolamin, globulin or albumin promoter from rice (Wu et al., Plant and Cell Physiology Vol. 39, No. 8 pp. 885–889 (1998)), a *Vicia faba* promoter from the legumin B4 and the unknown seed protein gene from *Vicia faba* described by Conrad U. et al, Journal of Plant Physiology Vol. 152, No. 6 pp. 708–711 (1998), a promotter from a seed oil body protein (Chen et al., Plant and cell physiology vol. 39, No. 9 pp. 935–941 (1998), the storage protein napA promoter from *Brassica napus*, or any other seed specific promoter known in the art, eg as described in WO 91/14772. Furthermore, the promoter may be a leaf specific promoter such as the rbcs promoter from rice or tomato (Kyozuka et al., Plant Physiology Vol. 102, No. 3 pp. 991–1000 (1993), the chlorella virus adenine methyltransferase gene promoter (Mitra, A. and Higgins, D W, Plant Molecular Biology Vol. 26, No. 1 pp. 85–93 (1994), or the aldP gene promoter from rice (Kagaya et al., Molecular and General Genetics Vol. 248, No. 6 pp. 668–674 (1995), or a wound inducible promoter such as the potato pin2 promoter (Xu et al, Plant Molecular Biology Vol. 22, No. 4 pp. 573–588 (1993).

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including Agrobacterium-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15–38), however it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992. Plant J. 2: 275–281; Shimamoto, 1994. Curr. Opin. Biotechnol. 5: 158–162; Vasil et al., 1992. Bio/Technology 10: 667–674). An alternative method for transformation of monocots is based on protoplast transformation as described by Omirulleh S, et al., Plant Molecular biology Vol. 21, No. 3 pp. 415–428 (1993).

Following transformation, the transformants having incorporated the expression construct are selected and regenerated into whole plants according to methods well-known in the art.

Methods of Production

The present invention also relates to methods for producing a polypeptide comprising (a) cultivating a host cell under conditions suitable for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO:1, 3, 5, 7, 9, or 11 wherein the mutant nucleic acid sequence encodes a polypeptide which consists of the amino acid sequence of the mature peptide of SEQ ID NO: 2, 4, 6, 8, 10, or 12, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Detergent Compositions Comprising the Enzymes and Variants of the Invention

The present invention comprises the use of the enzymes and variant enzymes of the invention in cleaning and detergent compositions and such compositions comprising the novel isolated RP-II proteases and RP-II protease variants or mutants. Such cleaning and detergent compositions are well described in the art and reference is made to WO 96/34946; WO 97/07202; WO 95/30011 for further description of suitable cleaning and detergent compositions.

Furthermore the example(s) below demonstrate the wash performance and improvements therein for a number of RP-II proteases and variants of the invention.

Detergent Compositions

The enzyme of the invention may be added to and thus ecome a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a further protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable further proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are RP-II proteases, and subtilisins, especially those derived from Bacillus, e.g. the RP-II proteases disclosed herein, and subtilisins, such as subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the wild type RP-II proteases and variants thereof described herein, and subtilisin variants described in WO 92/19729, WO 98/20115, WO 98/20116, and WO 98/34946, especially the subtilisin variants with substitutions in one or more of the following positions: 27, 36, 57, 76, 87, 97, 101, 104, 120, 123, 167, 170, 194, 206, 218, 222, 224, 235 and 274.

Commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

It was found that special synergistic advantages could be obtained by especially combinations comprising a RP-II protease and a subtilisin of the subtilase group I-S2 (Siezen et al. *Protein Science* 6 (1997) 501–523) or high alkaline subtilisins. Sub-group I-S2 proteases are described as highly alkaline subtilisins and comprises enzymes such as subtilisin PB92 (MAXACAL®, Gist-Brocades NV), subtilisin 309 (SAVINASE®, NOVO NORDISK A/S), subtilisin 147 (ESPERASE®, NOVO NORDISK A/S), and alkaline elastase YaB.

The combinations of BLC and JA96 and variants thereof with Savinase™ and variants thereof (e.g. Duralase™, Kannase™, Maxatase™, Maxacal™, Maxapem™, Properase™, Purafect™, Purafect OxP™, FN2™, and FN3™) were found to be especially useful in detergents.

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), *p. stutzeri* (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly (vinylpyrrolidone), poly (ethylene glycol), poly(vinyl alcohol), poly(vinyl-pyridine-N-oxide), poly (vinylimidazole), polycarboxylates such as polyacrylates, maleic/acrylic acid copolymers and lauryl methacrylate/ acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liquor, preferably 0.05–5 mg of enzyme protein per liter of wash liquor, in particular 0.1–1 mg of enzyme protein per liter of wash liquor.

Figure 2B:
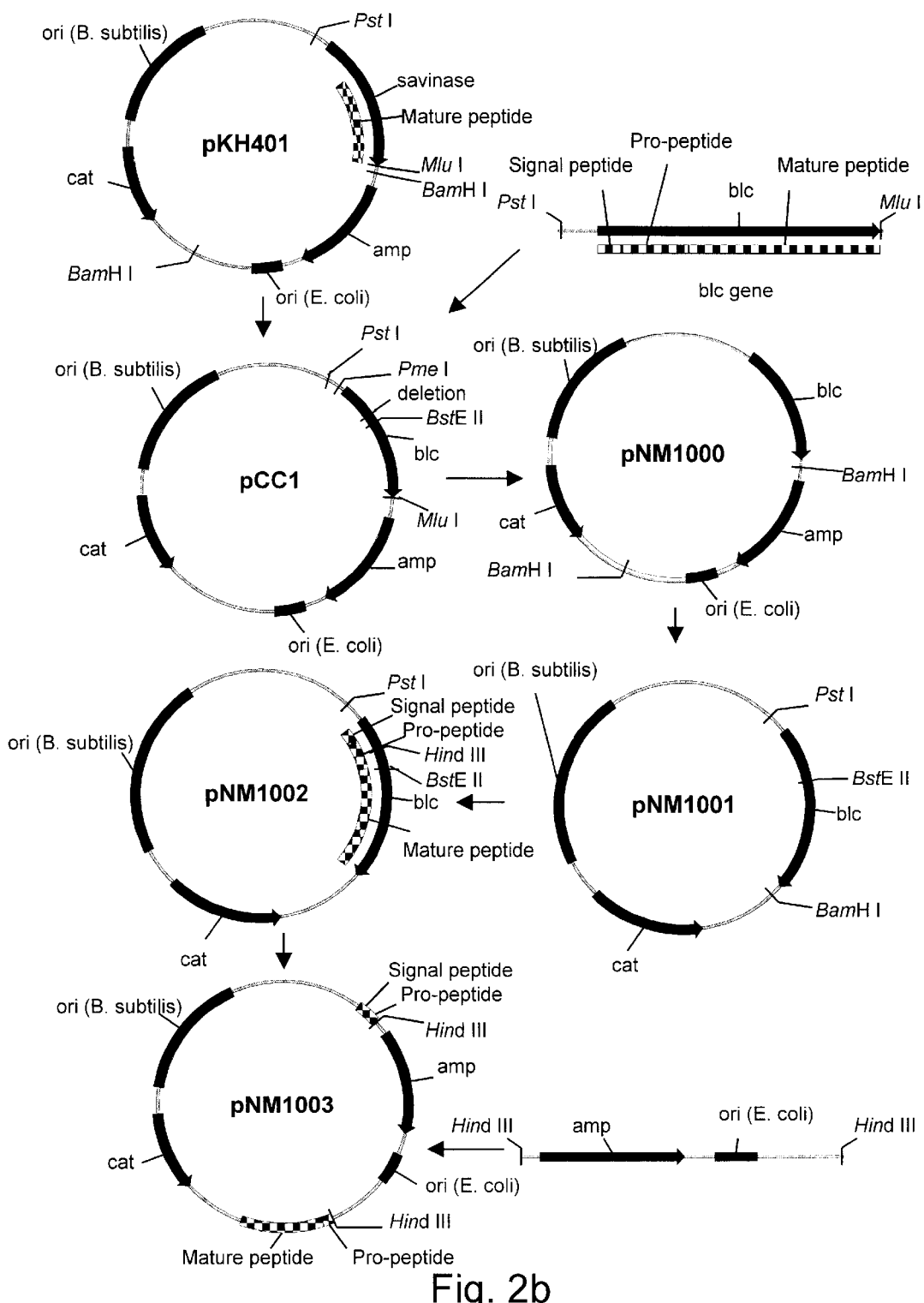

The enzyme of the invention may additionally be incorporated in the detergent formulations disclosed in WO 97/07202 which is hereby incorporated as reference.
Materials and Methods
Strains
  B. subtilis DN1885 (Diderichsen et al., 1990).
  B. lentus 309 and 147 are specific strains of Bacillus lentus, deposited with the NCIB and accorded the accession numbers NCIB 10309 and 10147, and described in U.S. Pat. No. 3,723,250 incorporated by reference herein.
  E. coli MC 1000 (M. J. Casadaban and S. N. Cohen (1980); J. Mol. Biol. 138 179–207), was made r−,m+ by conventional methods and is also described in U.S. patent application Ser. No. 039,298.
Plasmids
  pNM1003: E. coli—B. subtilis shuttle vector, derived from pSJ3 (Described by Jacob Schiødt et al. in Protein and Peptide letters 3:39–44 (1996)), containing a synthetic gene encoding for RP-II protease BLC. The construction of pNM1003 is indicated in FIG. 2.
  pNM1003EXP: B. subtilis BLC expression vector.
  pSX 222: B. subtilis expression vector (Described in WO 96/34946).
General Molecular Biology Methods
  Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA Manipulations
  Enzymes for DNA manipulations were used according to the specifications of the suppliers.
  Unless otherwise mentioned all enzymes for DNA manipulations, such as e.g. restriction endonucleases, ligases etc., are obtained from New England Biolabs, Inc.
Proteolytic Activity
  A GU is a Glycine Unit, defined as the proteolytic enzyme activity which, under standard conditions, during a 15 minutes' incubation at 40° C., with N-acetyl casein as substrate, produces an amount of $NH_2$-group equivalent to 1 mmole of glycine.
  RP-II protease activity can be measured using the PNA assay with succinyl-alanine-alanine-proline-glutamicacid-paranitroanilide as a substrate. The principle of the PNA assay is described in Rothgeb, T. M., Goodlander, B. D., Garrison, P. H., and Smith, L. A., Journal of the American Oil Chemists' Society, Vol. 65 (5) pp. 806–810 (1988).
Fermentation
  Fermentations for the production of the enzymes of the invention were performed at 37° C. on a rotary shaking table (300 r.p.m.) in 500 ml baffled Erlenmeyer flasks containing 100 ml PS-1 medium for 5 days.
  Consequently in order to make an e.g. 2 liter broth 20 Erlenmeyer flasks were fermented simultaneously.

EXAMPLE 1

Isolation of Wild Type Enzymes and Cloning of Wild Type Genes

An amino acid alignment of Glutamic Acid-specific protease (BLase) from Bacillus licheniformis ATCC 14580 (Kakudo, S., et.al J. Biol. Chem. 267:23782–23788 (1992)) and extracellular metalloprotease (mpr) (Sloma, A. et. al J. bacterial. 172: 1024–1029 (1990)) were made. Based on the alignment the following degenerate oligo nucleotide primers coding for conserved regions have been designed for molecular screening:
560 sense primer:
  5'-GGA TGG AGA AGC GGA AAC ACN AAY TAY GAY TAY GGN GC-3' (SEQ ID NO:18) corresponds to amino acids G-W-R-S-G-N-Y-D-Y-G (SEQ ID NO:19)
596 sense primer:
  5'-CCC AAG CTT GTX GYX ACN GCN GGN CAY T-3' (SEQ ID NO:20) corresponds to amino acids V-[A/V]-T-A-G-H (SEQ ID NO:21 ) with a CCC and Hind III site 5' tail.
566 antisense primer:
  5'-GAA TAC CGG TGA ACC GCT TTG NCM NCC RTA NGT RTC-3' (SEQ ID NO:22) corresponds to amino acids D-T-Y-G-[G/C/W/end]-Q-S-G-S-P-V-F (SEQ ID NO:23)
594 antisense primer:
  5'-GCT CTA GAG TYD ATN GCN CCR TAR TC-3' (SEQ ID NO:24) corresponds to amino acids D-Y-G-A-I-[E/K] (SEQ ID NO:25) with a GC and Xba I site 5' tail.
where N=A, C, G or T; R=A or G; Y=C or T; D=A,G or T; X=deoxyinosine.
  The genomic DNA from Bacillus strain AC116 and Bacillus strain CDJ31 were isolated according to the following procedure:
Procedure for Isolation of Genomic DNA
  1. Harvest 1.5 ml culture and resuspend in 100 μl TEL. Leave at 37 C. for 30 min.
  2. Add 500 μl Thiocynate buffer and leave at room temperature for 10 min.

3. Add 250 μl NH4Ac and leave at ice for 10 min.
4. Add 500 μl CIA and mix.
5. Transfer to a microcentrifuge and spin for 10 min. at full speed.
6. Transfer supernatant to a new Eppendorf tube and add 0.54 volume cold isopropanol. Mix thoroughly.
7. Spin and wash the DNA pellet with 70% EtOH.
8. Resuspend the genomic DNA in 100 μl TER.

TE
  10 mM Tris-HCl, pH 7.4
  1 mM EDTA, pH 8.0
TEL
  50 mg/ml Lysozym in TE-buffer
Thiocyanate
  5M guanidium thiocyanate
  100 mM EDTA 0.6% w/v N-laurylsarcosine, sodium salt.
  60 g thiocyanate, 20 ml 0.5 M EDTA, pH 8.0,
  20 mL H₂O dissolves at 65 C. Cool down to RT and add 0.6 g N-laurylsarcosine. Add H₂O to
  100 ml and filter it through a 0.2μ
  sterile filter.
NH₄Ac
  7.5 M CH₃COONH₄
TER
  1 μg/ml Rnase A in TE-buffer
CIA
  Chloroform/isoamyl alcohol 24:1

Experimental Procedure

Approximately 100 to 200 ng genomic DNA is used as template for PCR amplification in PCR buffer (10 mM Tris-HCl, pH 8.3, 50 mM KCl) containing 200 μM of each dNTP, 3.5 mM MgCl2, 2.5 Units AmpliTaq Gold™, and 100 pmol of each of the degenerate primers 594 and 596 or each of the degenerate primers 560 and 566. The total volume is 50 μl. The PCR reaction is carried out in a Perkin-Elmer GeneAmp PCR System 2400. The PCR reaction is performed using a cycle profile of:

| 94° C. - 10 min; | 1 cycle | | | |
|---|---|---|---|---|
| 94° C. - 1 min, | 60° C. - 1 min, | 72° C. - 30 sec; | 2 cycles |
| 94° C. - 1 min, | 59° C. - 1 min, | 72° C. - 30 sec; | 2 cycles |
| 94° C. - 1 min, | 58° C. - 1 min, | 72° C. - 30 sec; | 2 cycles |
| 94° C. - 1 min, | 52° C. - 1 min, | 72° C. - 30 sec; | 2 cycles |
| 94° C. - 1 min, | 50° C. - 1 min, | 72° C. - 30 sec; | 14 cycles |
| 72° C. - 7 min; | 1 cycles | | | |

5 μl aliquots of the amplification products are analysed by electrophoresis in 1.5% agarose gels.

Purification and Sequencing of PCR Bands

The PCR fragments can be purified and sequenced using GFXä PCR DNA and Gel Band Purification Kit (Pharmacia Biotech) according to the manufacturer's instructions. The nucleotide sequences of the amplified PCR fragments are determined directly on the purified PCR products using 200–300 ng as template, the Taq deoxy-terminal cycle sequencing kit (Perkin-Elmer, USA), fluorescent labelled terminators and 5 pmol of either sense or antisense primer on a ABI PRISM 377 DNA Sequencer, Perkin Elmer.

PCR fragments were generated on genomic DNA from Bacillus strain AC116 and Bacillus strain CDJ31 with primer set 594/596 and primer set 560/566, purified and sequenced as described above and the DNA sequence were deduced.

Sequence between primer 596 and 594 in the 596/594 PCR fragment from Bacillus strain AC116 (5'- to 3'-):
GCGTCTATGACACGGCAAGCCGATCATTCGCGG
GAACCGCCACCGTTTCCCCGGGACGAAACGGT
TCAGCTTACCCTTACGGATCTGTTACATCGA
CCCGCTATTTCATCCCGTCGGGTTGGCAGAGCG
GAAATTCCAATTAT (SEQ ID NO:26)
and translated into amino acid sequence:
CVYDTASRSFAGTATVSPGRNGSAY-
PYGSVTSTRYFIPSGWQSGNSNY (SEQ ID NO:27)
Sequence between primer 560 and 566 in the 560/566 PCR fragment from Bacillus strain AC116 (5'- to 3'-):
GATCGAGCTCAGCCAGCCGATCGGCAATACC
GTCGGATATTTCGGATATTCATACACCGCTTC
ATCGCTTGCAGGAGCAGGCGTGACCATCAGCG
GATATCCAGGAGACAAAACAACAGGCAC
CCAGTGGCAAATGTCCGGAACGATCGCT
GTTTCAGAAACGTATAAACTGCAATATGCGATC
(SEQ ID NO:28)
and translated into amino acid sequence:
IELSQPIGNTVGYFGYSYTASSLAGAGVTISGYPGD
KTTGTQWQMSGTIAVSETYKLQYAI (SEQ ID NO:29)
Sequence between primer 596 and 594 in the 596/594 PCR fragment from Bacillus strain CDJ31 (5'- to 3'-):
GCATTTATGACACAGCGAGCGGGTCATTCGCCGG
AACCGCTACCGTTTCTCCGGGACGGAACGGT
TCAACATATCCGTACGGATCAGTTACATCAAC
CCGCTATTTCATCCCGTCAGGCTATCGAAGC
GGAAATTCGAATTAC (SEQ ID NO:30)
and translated into amino acid sequence:
CIYDTASGSFAGTATVSPGRNGSTYPYGSVTST
RYFIPSGYRSGNSNY (SEQ ID NO:31)
Sequence between primer 560 and 566 in the 560/566 PCR fragment from Bacillus strain CDJ31 (5'- to 3'-):
CATAGAGCTCAGCCAGCCGATCGGCAACACC
GTCGGGTATTTCGGATATTCCTACACCACCTCG
TCTCTCGTTGGGTCAAGCGTTACCATCATCGG
ATATCCAGGCGACAAAACATCGGGCACCCAA
TGGCAGATGTCCGGAAATATCGCCGTCTC
AGAAACATATAAACTGCAATATGCGATC (SEQ ID NO:32)
and translated into amino acid sequence:
IELSQPIGNTVGYFGYSYTTSSLVGSSVTIIGYP
GDKTSGTQWQMSGNIAVSETYKLQYAI (SEQ ID NO:33)

Cloning by Inverse PCR

Based on the above DNA sequences oligo nucleotide primers were design for inverse PCR.
Bacillus strain AC116:
  602: 5'-CGT AAG GGT AAG CTG AAC C-3' (SEQ ID NO:34)
  603: 5'-CAG GAG ACA AAA CAA CAG CAG GC-3° (SEQ ID NO:35)
Bacillus strain CDJ31:
  598: 5'-GTC CCG GAG AAA CGG TAG-3' (SEQ ID NO:36)
  600: 5'-CAC CAC CTC GTC TCT CGT TG-5' (SEQ ID NO:37)
Method for Inverse PCR
1. Digested 0.5–1.0 mg genome DNA with BamHI, HindIII, KpnI, PstI, XbaI and XhoI respective in a volume of 50 ml over night at 37 C.
2. Purify the six DNA digests over a GFX Column according to manufactures instructions (GFX PCR DNA and Gel Band Purification Kit, Pharmacia Biotech).

3. Diluted to a final concentration of 1–10 mg/ml in ligase buffer. Add T4 ligase and incubated over night at 16 C.

4. Setup PCR as described with a long range PCR system. PCR condition for Expand Long Template PCR System from Boeringer Mannheim with a suspected fragment length at 4–6 kb:

1 ml of ligation mixture (template)

50 pmol of each primer (Tm should be between 63 C. and 68 C.)

1 ml 20 mM dNTP 5 ml 10× Buffer 1 with MgCl2

0.75 ml Expand DNA polymerase mix (Taq and Pwo)

H2O to 50 ml

Cycle profile: 1× (94 C. for 2 min.) 10× (94 C. for 10 s; 60 C. (depending of primer Tm) for 30 s; 68 C. for 4 min.)

20× (94 C. for 10 s; 60 C. for 30 s; 68 C. for 4 min.+20 s additional added per cycle)

1× (68 C. for 7 min.)

Gel purify the PCR products of interest (GFX) and the sequence of the gene can be determent. Based on the sequences new PCR primers for amplification and cloning of the gene can be design.

The same method were used for isolation of S2b proteases from Bacillus strain JA96, Bacillus strain BO32 and Bacillus strain AA513 with few modifications. New primers were design for molecular screening based on a new amino acid alignment containing the amino acid sequence from AC116 and CDJ31 (primer 611) and based on the N-terminal amino acid determination of the S2b protease from Bacillus strain C3371 (primer 646):

611 antisense primer:

5'-GCT CTA GAC GTY TTR TCX CMX GGR WAN CC-3' (SEQ ID NO:38) corresponds to amino acids G-[Y/F]-P-[G/C]-D-K-T (SEQ ID NO:39) with a GC and Xba I site 5' tail.

646 sense primer:

5'-CCC AAG CTT GTX GTX ATH GGX GAY GAY GG-3 (SEQ ID NO:40) corresponds to amino acids V-V-I-G-G-D-D-G (SEQ ID NO:41) with a CCC and Hind III site 5' tail.

The 611/646 primer set were used as described above on genomic DNA from Bacillus strain JA96, Bacillus strain BO32 and Bacillus strain AA513 isolated as described above. Sequence determination of the PCR fragments, design of primers for inverse PCR, inverse PCR reactions and sequencing of the genes were done as described above.

All five genes were cloned into the pUC19 vector and transformed into the *Escherichia coli* strain DH10B (Life Technologies) and deposited with DSM as indicated above. DSM 12841: *E. coli* pUC19/AC116, DSM 12842: *E. coli* pUC/CDJ31 DSM 12843: *E. coli* pUC/BO32, DSM 12844: *E. coli* pUC/JA96 DSM 12845: *E. coli* pUC/AA513

The DNA sequences and the amino acid sequences derived therefrom are indicated in SEQ ID. NOS. 1 to 12.

The coding region of the genes can be excised from the pUC19 constructions and subcloned into a Bacillus expression vector such as pNM1003exp, and further transformed into *B. subtilis* DN1885 for expression of the novel isolated RP-II proteases of the invention as described in Example 2.

EXAMPLE 2

Construction and Expression of Enzyme Variants

A *B. subtilis-E.coli* shuttle vector, pNM1003, suited to a gene coding for RP-II protease BLC and its mutants was constructed. It is derived from the *B. subtilis* expression vector pSX222 (Described in WO 96/34946) according to flowchart shown in FIGS. 2a and 2b and as described below.

pKH400

A DNA fragment from pJS3 encoding the beta-lactamase gene and oriC was prepared by PCR using primers introducing BamHI sites in the fragment terminals. The PCR product was digested with BamHI and ligated with BamHI digested pSX222. The ligation mixture were used to transform competent *E. coli* MC1000 r$^-$ m$^+$, selecting for ampicillin resistance.

pKH401

A PstI site was introduced by site directed mutagenesis in the upstream region of the gene encoding savinase.

pCC1 pKH401 was restricted with PstI and MluI in order to remove the gene encoding subtilisin 309. A 5174 bp PstI-MluI pKH401 vector fragment was ligated with a PstI-MluI DNA fragment encoding BLC. Such DNA can be obtained in a manner as described in EP 482 879. The ligation mixture were used to transform competent *E. coli* MC1000 r$^-$ m$^+$. A plasmid (pCC1) with a single nucleotide deletion in the BLC gene was isolated since expression of BLC in *E. coli* is toxic. The single nucleotide deletion was located in the pro-peptide region of BLC.

pNM1000

A PmeI-BstEII fragment of pCC1 was replaced by a 343 bp RsaI-BstEII fragment from a wt BLC gene. The ligation mixture were used to transform competent *B. subtilis* DN1885 selecting for protease activity. Plasmid DNA was isolated and verified by sequencing.

Plasmid pNM1001 pNM1000 were restricted with BamHI and the 4350 bp large fragment was isolated. The 4350 bp fragment was ligated an d the ligation mixture was used to transform competent *B. subtilis* DN1885 selecting for protease activity. Plasmid DNA was isolated and verified by DNA sequencing.

Plasmid pNM1002

A PCR product covering the region PstI-BstEII of pNM1001, introducing a HindIII site by site-directed mutagenesis in the propeptide region BLC gene, was restricted with PstI-BstEII and ligated to a 3925 bp PstI-BstEII fragment of pNM1001. The ligation mixture was used to transform competent *B. subtilis* DN1885 selecting for protease activity. Plasmid DNA was isolated and verified by DNA sequencing.

Plasmid pNM1003

The ampicillin gene and oriC region of pNM1000 were amplified by PCR using primers introducing HindIII sites in the terminals. The PCR product was restricted with HindIII and ligated to HindIII restricted pNM1002. The ligation mixture was used to transform competent *E. coli* MC1000 r$^-$ m$^+$, selecting for ampicillin resistance. Plasmid DNA was isolated and confirmed by sequencing.

pNM1003EXP pNM1003 was restricted with HindIII and a 4350 bp DNA fragment was isolated and ligated. The ligation mixture were used to transform competent *B. subtilis* DN1885, selecting for protease activity.

Site-Directed Mutagenesis

BLC site-directed variants of the invention comprising specific substitutions, insertions or deletions in the molecule were made by traditional cloning of DNA fragments (Sambrook et al., Molecular Cloning: A Laboratory Manual, 2nd Ed., Cold Spring Harbor, 1989) produced by PCR of oligos containing the desired insertions (see below).

The template plasmid DNA was pNM1003, or an analogue of this containing a variant of RP-II protease BLC.

Insertions were introduced by oligo directed mutagenesis to the construction of substitution, insertion or deletion variants resulting in RP-II BLC variants.

The BLC variants were transformed into *E. coli*. DNA purified from a over night culture of these transformants were transformed into *B. subtilis* by restriction endonuclease digestion, purification of DNA fragments, ligation, transformation of *B. subtilis*. Transformation of *B. subtilis* was performed as described by Dubnau et al., 1971, J. Mol. Biol. 56, pp. 209–221.

Localized Random Mutagenesis in Order to Insert Random Insertions in a Localized Region The overall strategy used to perform localized random mutagenesis was:

a mutagenic primer (oligonucleotide) was synthesized, that corresponds to the DNA sequence flanking the site of substitution, insertion or deletion, separated by the DNA base pairs defining the substitution, insertion or deletion.

Subsequently, the resulting mutagenic primer was used in a PCR reaction with a suitable opposite primer. The resulting PCR fragment was purified and extended in a second PCR-reaction, before being digested by endonucleases and cloned into the *E. coli–B. subtilis* shuttle vector (see below).

Alternatively, and if necessary, the resulting PCR fragment is used in a second PCR reaction as a primer with a second suitable opposite primer to allow digestion and cloning of the mutagenized region into the shuttle vector. The PCR reactions are performed under normal conditions.

Following this strategy a localized random library was constructed in BLC wherein substitutions were introduced at position 36.

The mutations were introduced by mutagenic primers (see below), so that all 20 amino acids, except Trp and Met, are represented (N=25% of A, T, C, and G; whereas H=33% A, 33% C and 33% T. The produced PCR fragment were extended towards the N-terminal of BLC by another round of PCR by combination of a overlapping sequence with a PCR-fragment produced by PCR-amplification with primers; 5' CGG ACC GTT GCA GTT CGT TCT GGA GC 3' (sense) (SEQ ID NO:42) and 5' CCG GCA AAG TGA ATG AAA CAA AGG AAA AAG CGG 3' (anti-sense) (SEQ ID NO:43). The extended DNA-fragments were cloned into the BstE II- and PinA I- sites of the modified plasmid pNM1003 (see above), and ten randomly chosen *E. coli* colonies were sequenced to confirm the mutations designed.

The mutagenic primer (5' A TGC ACC GGA TGG NNH ATA GGT CCG AAA ACC 3' (anti-sense) (SEQ ID NO:44) were used in a PCR reaction with a suitable sense opposite primer, situated downstream of the Mlu I site in pNM1003 (e.g. 5'-CCC TTT AAC CGC ACA GCG TTT-3' (anti-sense)) (SEQ ID NO:45) and the plasmid pNM1003 as template. This resulting PCR product was cloned into the pNM1003 shuttle vector by using the restriction enzymes BstE II and PinA I.

The random library was transformed into *E. coli* by well known techniques. The library prepared contained approximately 100,000 individual clones/library. Ten randomly chosen colonies were sequenced to confirm the mutations designed.

In order to purify a BLC variant of the invention, the pNM1003EXP plasmid comprising a variant of the invention was created by digestion of pNM1003 with HindIII, ligated and transformed into a competent *B. subtilis* strain, selecting for protease activity, and was fermented as described above in a medium containing 10 μg/ml Chloramphenicol (CAM).

EXAMPLE 3

Purification of Enzymes and Variants

This procedure relates to purification of a 2 liter scale fermentation for the production of the proteases of the invention in a Bacillus host cell.

Approximately 1.6 liters of fermentation broth were centrifuged at 5000 rpm for 35 minutes in 1 liter beakers. The supernatants were adjusted to pH 7 using 10% acetic acid and filtered through a Seitz Supra S100 filter plate.

At room temperature, the filtrate was applied to a 100 ml Bacitracin affinity column equilibrated with 0.01 M dimethylglutaric acid, 0.1 M boric acid and 0.002 M calcium chloride adjusted to pH 7 with sodium hydroxide (Buffer A). After washing the column with Buffer A to remove unbound protein, the protease was eluted from the Bacitracin column using Buffer A supplemented with 25% 2-propanol and 1 M sodium chloride.

The fractions with proteolytic activity from the Bacitracin purification step were combined and applied to a 750 ml Sephadex G25 column (5 cm dia.) equilibrated with Buffer A.

Fractions with proteolytic activity from the Sephadex G25 column were combined and the pH was adjusted to pH 6 with 10% acetic acid and applied to a 150 ml CM Sepharose CL 6B cation exchange column (5 cm dia.) equilibrated with a buffer containing 0.01 M dimethylglutaric acid, 0.1 M boric acid, and 0.002 M calcium chloride adjusted to pH 6 with sodium hydroxide.

The protease was eluted using a linear gradient of 0–0.2 M sodium chloride in 2 liters of the same buffer.

Finally, the protease containing fractions from the CM Sepharose column were combined and filtered through a 0.2 μm filter.

By using the techniques of Example 1 for the isolation of wild type enzymes, and the above isolation procedure the RP-II proteases indicated below were produced and isolated.

For ease of reference the wild type RP-II proteases have in FIGS. 1a to 1c been aligned to the RP-II protease from *Bacillus licheniformis*, BCL, in the manner described above to establish the numbering of the amino acid residues.

By using the techniques of Example 2 for the construction of variants and fermentation, and the above isolation procedure the following RP-II protease variants of the BLC protease were produced and isolated:

D6A
D7A
D7G+T125S+E152G+N182I
S28R
S28R+T80K
S28R+Q157R
S28R+E152V
S28R+E152A+E209A
S28R+T80K+Q157R
I29A
I29A+E152A
I29A+E152A+E209A
D51A
D51A+E152A
D51N+V77I+T137R+R144H
G59R+I150T
T62S+E152G+Q174R+T179S
G69R
G69R+S76T
T80K
T80K+Q157R
T80K+E152A+E209A
Y95F+E209K

E101A
E101+E173A+E209A
E104A
E104K
E104A+E152A
E104A+E152A+E209A
E104A+E152A+V189I
E104K+Q174R+S186A
D135A
H141A
E152A
E152K
E152G
E152V
E152A+D212A
E152A+E173A
E152A+E209A
E152A+V189L
E152G+G164R
E152K+A159S+E173D
Y154F+Q157R
Q157R
Q157R+E152A+E209A
M160A
D161A
T162M
S167A
E173A
Q174R
V189I
H190M
T191S
N192*
E209A
E209K
D212A

These variants exhibited better wash performance than the RP-II protease BLC in a preliminary assay.

EXAMPLE 4
Wash Performance of Protease Variants (I)

The following examples provide results from a number of washing tests that were conducted under the conditions indicated below.

Experimental Conditions

TABLE 1

| Experimental setup. | |
| --- | --- |
| Detergent | OMO color, 4.0 g/l |
| pH | 10.25 |
| Water hardness | 18° dH ~ 3.22 mM $Ca^{2+}/Mg^{2+}$ |
| Wash time | 20 min. |
| Temperature | 30° C. |
| Enzyme conc. | 10 nM |
| Test system | 150 ml beakers with a stirring rod |
| Test material | 5 pieces of test material (Ø 2.5 cm) in 50 ml detergent solution |

Water hardness was adjusted by adding $CaCl_2$ and $MgCl_2$ to deionized water.

Detergent

The detergent used were obtained from a supermarket in Bagsvaerd, Denmark. Prior to use all enzymatic activity in the detergent was inactivated by micro wave treatment.

Test Materials

The test material used were EMPA116 (obtained from EMPA Testmaterials, Movenstrasse 12, CH-9015 St. Gallen, Switzerland), and cotton soiled with grass juice.

Reflectance

Reflectance measurements of the test materials were done at 460 nm using a J&M Tidas MMS/16 photometer equipped with a CLX 75W Xenon lamp and fibre optics. Each textile piece was measured individually with other textile pieces (same settings) as background.

Evaluation

The evaluation of the wash performance of the RP-II proteases was performed by measuring the reflectance of test material washed with said RP-II proteases. High reflectance values mean that the test material was cleaned, and indicate an improved RP-II protease wash performance.

SAS 6.12 software was used to make an analysis of variance and a t-test comparison (Student-Newman-Keuls) at 95% significance on the experimental data.

Results

The capital letters designate statistical groupings within each column based on a t-test. If two variants are in the same group (same letter), they cannot be separated statistically.

TABLE 2

| Mean reflectance for each variant. | | | | |
| --- | --- | --- | --- | --- |
| Enzyme | EMPA116 | | Grass | |
| E152A | 24.5 | A | 51.8 | C |
| E152A + E209A | 24.5 | A | 53.4 | A |
| E152A + I29T | 24.5 | A | 51.0 | D |
| E152A + V144L | 24.2 | A | 52.7 | B |
| E152A + I29S | 24.1 | B | 51.1 | D |
| E104A | 23.8 | B | 51.1 | D |
| E152A + I29A | 23.6 | C | 50.3 | D |
| E173A | 23.4 | D | 50.2 | E |
| E209A | 23.3 | D | 51.5 | C |
| D212A | 22.4 | E | 49.9 | E |
| V189I | 22.1 | E | 48.0 | F |
| BLC | 21.9 | E | 47.3 | G |
| Blind | 19.4 | F | 45.9 | G |
| Root MSE | 0.4 | | 0.5 | |
| R-square | 0.96 | | 0.97 | |

EXAMPLE 5
Wash Performance of Protease Variants (II)

Experimental Conditions

The washing tests were conducted under the same experimental conditions as described in Example 3.

Evaluation

Evaluation of the RP-II proteases was done as in Example 3, except that no statistical analysis was carried out.

Results

The reflectance measurements are shown in table 3 below.

TABLE 3

| Mean reflectance for each variant. | | |
| --- | --- | --- |
| Enzyme | EMPA116 | Grass |
| E104K | 24.2 | 50.7 |
| T62S + E152G | 24.2 | 50.5 |
| E104K + Q204R | 23.7 | 50.6 |
| E209R | 23.7 | 50.2 |
| Y154K + Q157R | 22.5 | 46.4 |
| T80K + Q157R | 22.4 | 47.8 |
| BLC | 21.9 | 47.3 |
| Blind | 19.4 | 45.9 |

What is claimed is:

1. A protease variant comprising a mutation in an amino acid sequence of amino acids 1–222 of SEQ ID NO: 2, wherein the mutation comprises at least one of the following:

(a) a modification of an Asn-Gly sequence by substitution, deletion and/or insertion to change or remove the Asn-Gly sequence, (b) a substitution or deletion of an aspartate or glutamate at one or more positions selected from the group consisting of D6, D7, D51, E101, E104, D135, E152, D161, E173, E209, and D212;

(c) a deletion or substitution of a methionine;

(d) a deletion or substitution of a tryptophan located at the surface;

(e) a substitution of a tyrosine located at the surface;

(f) a substitution of an amino acid occupying the first and/or second position following Glu or Asp with Pro; and (g) a modification selected from the group consisting of S28R, I29A, G59R, T62S, S76T, V77I, T80K, H141A, T125S, I129A, T137R, R144H, I150T, Q157R, A159S, T162M, G164R, S167A, Q174R, T179S, N182I, S186A, V189I, V189L, H190M, and T191S.

2. A protease variant of claim 1, comprising a modification of an Asn-Gly sequence by substitution, deletion and/or insertion to change or remove the Asn-Gly sequence.

3. A protease variant of claim 2, comprising a modification selected from the group consisting of:

N68{A,Q,S,P,T,Y};
N68{A,Q,S,P,T,Y}+G69{A,Q,S,P,T,Y};
G69{A,Q,S,P,T,Y};
N192{A,Q,S,P,T,Y};
N 192{A,Q,S,P,T,Y}+G193{A,Q,S,P,T,Y}; and
G193{A,Q,S,P,T,Y}.

4. A protease variant of claim 3, comprising a substitution or deletion of an aspartate or glutamate at one or more positions selected from the group consisting of: D6, D7, D51, E101, E104, D135, E152, D161, E173, E209, and D212.

5. A protease variant of claim 4, comprising D6A, D7A, D51A, E101A, E104A, D135A, E152A, D161A, E173A, E209A, D212A, or any combination thereof.

6. A protease variant of claim 1, comprising a substitution of an amino acid occupying the first and/or second position following any Glu or Asp with Pro.

7. The protease variant of claim 6, comprising the modification Q174P; S175P; or Q174P+S175P.

8. A protease variant of claim 1, comprising a deletion or substitution of a methionine.

9. A protease variant of claim 8, wherein the methionine is substituted with A, E, I, K, L, N, Q, or S.

10. A protease variant of claim 9, comprising M36{A,K,N,Q,S} or M160{A,K,N,Q,S}.

11. A protease variant of claim 1, comprising a deletion or substitution of a tryptophan located at the surface.

12. A protease variant of claim 11, comprising a substitution of tryptophan with F, G, Q, or T.

13. A protease variant of claim 12, comprising W35{F,G,Q,T}; W88{F,G,Q,T}; W142{F,G,Q,T}; or W217{F,G,Q,T}.

14. A protease variant of claim 1, comprising a substitution of a tyrosine located at the surface.

15. A protease variant of claim 14, comprising a substitution of Tyr with Phe or Trp.

16. A protease variant of claim 15, comprising Y17{F,W}; Y19{F,W}; Y50{F,W}; Y72{F,W}; Y74{F,W}; Y82{F,W}; Y95{F,W}; Y97{F,W}; Y112{F,W}; Y115{F,W}; Y117{F,W}; Y132{F,W,}; Y154{F,W}; Y158{F,W}; Y163{F,W}; Y195{F,W}; or Y200{F,W}.

17. A protease variant of claim 1 comprising E152{G,K,R}.

18. A protease variant of claim 1, comprising at least one modification from the group consisting of: D6A; D7A; D7G+T125S+E152G+N182I; S28R; S28R+T80K; S28R+T80K+Q157R; S28R+E152A+E209A; S28R+E152V; S28R+Q157R; I29A; I29A+E152A; I29A+E152A+E209A; D51A; D51A+E152A; D51N+V77I+T137R+R144H; G59R+I150T; T62S+E152G+Q174R+T179S; G69R; G69R+S76T; T80K; T80K+E152A+E209A; T80K+Q157R; Y95F+E209K; E101A; E101A+E173A+E209A; E104A; E104A+E152A; E104A+E152A+V189I; E104A+E152A+E209A; E104K; E104K+Q174R+S186A; D135A; H141A; E152A; E152A+E173A; E152A+V189L; E152A+E209A; E152A+D212A; E152G; E152G+G164R; E152K; E152K+A159S+E173D; E152V; Y154F+Q157R; Q157R; Q157R+E152A+E209A; M160A; D161A; T162M; S167A; E173A; Q174R; V189I; H190M; T191S; N192*; E209A; E209K; and D212A.

19. A detergent composition, comprising a protease variant of claim 1 and a surfactant.

20. The detergent composition of claim 19, further comprising one or more additional enzymes selected from the group consisting of amylase, cellulase, lipase, oxidase, peroxidase, and another protease.

21. A nucleic acid sequence encoding a protease variant of claim 1.

22. A nucleic acid construct comprising a nucleic acid sequence of claim 21 operably linked to one or more control sequences which direct the production of the protease variant in a suitable expression host.

23. A recombinant expression vector comprising a nucleic acid construct of claim 22, a promoter, and transcriptional and translational stop signals.

24. A recombinant host cell comprising a recombinant expression vector of claim 23.

25. A method for producing a protease variant, comprising (a) cultivating the recombinant host cell of claim 24 under conditions suitable for production of the protease variant; and (b) recovering the protease variant.

26. A detergent composition comprising a protease having an amino acid sequence of amino acids 1–222 of SEQ ID NO: 2 and a surfactant.

27. The detergent composition of claim 26, further comprising one or more additional enzymes selected from the group consisting of amylase, cellulase, lipase, oxidase, peroxidase, and another protease.

* * * * *

SEQUENCE LISTING

<160> NUMBER OF SEQ ID NOS: 14

<210> SEQ ID NO 1
<211> LENGTH: 948
<212> TYPE: DNA
<213> ORGANISM: Bacillus licheniformis
<220> FEATURE:
<221> NAME/KEY: CDS
<222> LOCATION: (1)..(948)
<220> FEATURE:
<221> NAME/KEY: sig_peptide
<222> LOCATION: (1)..(93)
<220> FEATURE:
<221> NAME/KEY: pro-peptide
<222> LOCATION: (94)..(282)
<220> FEATURE:
<221> NAME/KEY: mat_peptide
<222> LOCATION: (283)..()

<400> SEQUENCE: 1

```
ttg gtt agt aaa aag agt gtt aaa cga ggt ttg atc aca ggt ctc att        48
Leu Val Ser Lys Lys Ser Val Lys Arg Gly Leu Ile Thr Gly Leu Ile
            -90                 -85                 -80 ggt att tct att tat tct tta ggt atg cac ccg gcc caa gcc gcg cca        96
Gly Ile Ser Ile Tyr Ser Leu Gly Met His Pro Ala Gln Ala Ala Pro
        -75                 -70                 -65 tcg cct cat act cct gtt tca agc gat cct tca tac aaa gcg gaa aca       144
Ser Pro His Thr Pro Val Ser Ser Asp Pro Ser Tyr Lys Ala Glu Thr
    -60                 -55                 -50 tcg gtt act tat gac cca cac att aag agc gat caa tac ggc ttg tat       192
Ser Val Thr Tyr Asp Pro His Ile Lys Ser Asp Gln Tyr Gly Leu Tyr
-45                 -40                 -35 tca aaa gcg ttt aca ggc acc ggc aaa gtg aat gaa aca aag gaa aaa       240
Ser Lys Ala Phe Thr Gly Thr Gly Lys Val Asn Glu Thr Lys Glu Lys
-30                 -25                 -20                 -15 gcg gaa aaa aag tca ccc gcc aaa gct cct tac agc att aaa tcg gtg       288
Ala Glu Lys Lys Ser Pro Ala Lys Ala Pro Tyr Ser Ile Lys Ser Val
            -10                  -5                  -1   1 att ggt tct gat gat cgg aca agg gtc acc aac aca acc gca tat ccg       336
Ile Gly Ser Asp Asp Arg Thr Arg Val Thr Asn Thr Thr Ala Tyr Pro
          5                  10                  15 tac aga gcg atc gtt cat att tca agc agc atc ggt tca tgc acc gga       384
Tyr Arg Ala Ile Val His Ile Ser Ser Ser Ile Gly Ser Cys Thr Gly
 20                  25                  30 tgg atg atc ggt ccg aaa acc gtc gca aca gcc gga cac tgc atc tat       432
Trp Met Ile Gly Pro Lys Thr Val Ala Thr Ala Gly His Cys Ile Tyr
35                  40                  45                  50 gac aca tca agc ggt tca ttt gcc ggt aca gcc act gtt tcg ccg gga       480
Asp Thr Ser Ser Gly Ser Phe Ala Gly Thr Ala Thr Val Ser Pro Gly
                 55                  60                  65 cgg aac ggg aca agc tat cct tac ggc tca gtt aaa tcg acg cgc tac       528
Arg Asn Gly Thr Ser Tyr Pro Tyr Gly Ser Val Lys Ser Thr Arg Tyr
             70                  75                  80 ttt att ccg tca gga tgg aga agc gga aac acc aat tac gat tac gga       576
Phe Ile Pro Ser Gly Trp Arg Ser Gly Asn Thr Asn Tyr Asp Tyr Gly
         85                  90                  95 gca atc gaa cta agc gaa ccg atc ggc aat act gtc gga tac ttc gga       624
Ala Ile Glu Leu Ser Glu Pro Ile Gly Asn Thr Val Gly Tyr Phe Gly
    100                 105                 110 tac tcg tac act act tca tca ctt gtt ggg aca act gtt acc atc agc       672
Tyr Ser Tyr Thr Thr Ser Ser Leu Val Gly Thr Thr Val Thr Ile Ser
115                 120                 125                 130
```

```
ggc tac cca ggc gat aaa aca gca ggc aca caa tgg cag cat tca gga      720
Gly Tyr Pro Gly Asp Lys Thr Ala Gly Thr Gln Trp Gln His Ser Gly
            135                 140                 145 ccg att gcc atc tcc gaa acg tat aaa ttg cag tac gca atg gac acg      768
Pro Ile Ala Ile Ser Glu Thr Tyr Lys Leu Gln Tyr Ala Met Asp Thr
        150                 155                 160 tac gga gga caa agc ggt tca ccg gta ttc gaa caa agc agc tcc aga      816
Tyr Gly Gly Gln Ser Gly Ser Pro Val Phe Glu Gln Ser Ser Ser Arg
        165                 170                 175 acg aac tgt agc ggt ccg tgc tcg ctt gcc gta cac aca aat gga gta      864
Thr Asn Cys Ser Gly Pro Cys Ser Leu Ala Val His Thr Asn Gly Val
        180                 185                 190 tac ggc ggc tcc tcg tac aac aga ggc acc cgg att aca aaa gag gtg      912
Tyr Gly Gly Ser Ser Tyr Asn Arg Gly Thr Arg Ile Thr Lys Glu Val
195                 200                 205                 210 ttc gac aat ttg acc aac tgg aaa aac agc gca caa                      948
Phe Asp Asn Leu Thr Asn Trp Lys Asn Ser Ala Gln
            215                 220

<210> SEQ ID NO 2
<211> LENGTH: 316
<212> TYPE: PRT
<213> ORGANISM: Bacillus licheniformis

<400> SEQUENCE: 2

Leu Val Ser Lys Lys Ser Val Lys Arg Gly Leu Ile Thr Gly Leu Ile
                -90                 -85                 -80

Gly Ile Ser Ile Tyr Ser Leu Gly Met His Pro Ala Gln Ala Ala Pro
            -75                 -70                 -65

Ser Pro His Thr Pro Val Ser Ser Asp Pro Ser Tyr Lys Ala Glu Thr
        -60                 -55                 -50

Ser Val Thr Tyr Asp Pro His Ile Lys Ser Asp Gln Tyr Gly Leu Tyr
    -45                 -40                 -35

Ser Lys Ala Phe Thr Gly Thr Gly Lys Val Asn Glu Thr Lys Glu Lys
-30                 -25                 -20                 -15

Ala Glu Lys Lys Ser Pro Ala Lys Ala Pro Tyr Ser Ile Lys Ser Val
                -10                 -5                  -1  1

Ile Gly Ser Asp Asp Arg Thr Arg Val Thr Asn Thr Thr Ala Tyr Pro
        5                   10                  15

Tyr Arg Ala Ile Val His Ile Ser Ser Ser Ile Gly Ser Cys Thr Gly
    20                  25                  30

Trp Met Ile Gly Pro Lys Thr Val Ala Thr Ala Gly His Cys Ile Tyr
35                  40                  45                  50

Asp Thr Ser Ser Gly Ser Phe Ala Gly Thr Ala Thr Val Ser Pro Gly
            55                  60                  65

Arg Asn Gly Thr Ser Tyr Pro Tyr Gly Ser Val Lys Ser Thr Arg Tyr
        70                  75                  80

Phe Ile Pro Ser Gly Trp Arg Ser Gly Asn Thr Asn Tyr Asp Tyr Gly
        85                  90                  95

Ala Ile Glu Leu Ser Glu Pro Ile Gly Asn Thr Val Gly Tyr Phe Gly
        100                 105                 110

Tyr Ser Tyr Thr Thr Ser Ser Leu Val Gly Thr Val Thr Ile Ser
115                 120                 125                 130

Gly Tyr Pro Gly Asp Lys Thr Ala Gly Thr Gln Trp Gln His Ser Gly
            135                 140                 145

Pro Ile Ala Ile Ser Glu Thr Tyr Lys Leu Gln Tyr Ala Met Asp Thr
```

```
                      150                 155                 160
Tyr Gly Gly Gln Ser Gly Ser Pro Val Phe Glu Gln Ser Ser Ser Arg
                165                 170                 175

Thr Asn Cys Ser Gly Pro Cys Ser Leu Ala Val His Thr Asn Gly Val
        180                 185                 190

Tyr Gly Gly Ser Ser Tyr Asn Arg Gly Thr Arg Ile Thr Lys Glu Val
195                 200                 205                 210

Phe Asp Asn Leu Thr Asn Trp Lys Asn Ser Ala Gln
                215                 220

<210> SEQ ID NO 3
<211> LENGTH: 1026
<212> TYPE: DNA
<213> ORGANISM: Bacillus halmapalus AA513
<220> FEATURE:
<221> NAME/KEY: CDS
<222> LOCATION: (1)..(1026)
<220> FEATURE:
<221> NAME/KEY: sig_peptide
<222> LOCATION: (1)..(78)
<220> FEATURE:
<221> NAME/KEY: pro-peptide
<222> LOCATION: (79)..(360)
<220> FEATURE:
<221> NAME/KEY: mat_peptide
<222> LOCATION: (361)..()

<400> SEQUENCE: 3 atg aaa cta cta tta aaa ctt act ttt gta tgc ata ttt atg tta          45
Met Lys Leu Leu Leu Lys Leu Thr Phe Val Cys Ile Phe Met Leu
-120             -115                 -110 agt ggg att cta tcc cca gta aac gca act caa gct gag act ctt act     93
Ser Gly Ile Leu Ser Pro Val Asn Ala Thr Gln Ala Glu Thr Leu Thr
    -105                 -100                 -95                 -90 aaa tta aat aaa ata agt cag aag cag gaa cca tca tat aaa cta gat    141
Lys Leu Asn Lys Ile Ser Gln Lys Gln Glu Pro Ser Tyr Lys Leu Asp
                -85                 -80                 -75 gaa gaa atg gat tat gtt cta att gat ttg gaa aca caa tct gaa tcg    189
Glu Glu Met Asp Tyr Val Leu Ile Asp Leu Glu Thr Gln Ser Glu Ser
        -70                 -65                 -60 att att tcg ata gga gat aat acc gat ttg gga gat caa tcg ttt act    237
Ile Ile Ser Ile Gly Asp Asn Thr Asp Leu Gly Asp Gln Ser Phe Thr
    -55                 -50                 -45 tct tta ggg aag gtg gga cat gga gaa ctt gag aaa att aac tta gaa    285
Ser Leu Gly Lys Val Gly His Gly Glu Leu Glu Lys Ile Asn Leu Glu
        -40                 -35                 -30 gaa ttt cgt aat cct aat tta aca gta gta gac ccg tta aca cgt aag    333
Glu Phe Arg Asn Pro Asn Leu Thr Val Val Asp Pro Leu Thr Arg Lys
-25                 -20                 -15                 -10 cct att gaa caa aaa atc agc cct ttt gtt gtt ata ggc gat gat ggg    381
Pro Ile Glu Gln Lys Ile Ser Pro Phe Val Val Ile Gly Asp Asp Gly
            -5              -1  1                   5 aga aga caa gtt caa aat act tct ttc atg cca ttt cgt gca ctt act    429
Arg Arg Gln Val Gln Asn Thr Ser Phe Met Pro Phe Arg Ala Leu Thr
            10                  15                  20 tat att gag ttt gga aac ctt aca agt aca tgg agt tgt tct gga ggt    477
Tyr Ile Glu Phe Gly Asn Leu Thr Ser Thr Trp Ser Cys Ser Gly Gly
        25                  30                  35 gtg att gga aca gat tta gtt gtt act aat gca cat tgt gta gaa ggt    525
Val Ile Gly Thr Asp Leu Val Val Thr Asn Ala His Cys Val Glu Gly
40                  45                  50                  55 tct gtg tta gca ggt act gta gtt cct ggt atg aac aat agt cag tgg    573
```

```
Ser Val Leu Ala Gly Thr Val Val Pro Gly Met Asn Asn Ser Gln Trp
                60                  65                  70 gca tat ggg cat tat agg gtt act cag att atc tac cct gat caa tac          621
Ala Tyr Gly His Tyr Arg Val Thr Gln Ile Ile Tyr Pro Asp Gln Tyr
             75                  80                  85 aga aat aac ggt gct tca gag ttt gat tat gct ata ctt aga gta gca          669
Arg Asn Asn Gly Ala Ser Glu Phe Asp Tyr Ala Ile Leu Arg Val Ala
         90                  95                 100 cct gac tct gat gga cgt cat att gga aac aga gct gga att tta tct          717
Pro Asp Ser Asp Gly Arg His Ile Gly Asn Arg Ala Gly Ile Leu Ser
        105                 110                 115 ttt aca gaa aca gga act gtt aac gaa aat act ttt cta aga acg tat          765
Phe Thr Glu Thr Gly Thr Val Asn Glu Asn Thr Phe Leu Arg Thr Tyr
120                 125                 130                 135 gga tac ccc ggt gat aaa ata tca gag aca aaa tta att tct ttg tgg          813
Gly Tyr Pro Gly Asp Lys Ile Ser Glu Thr Lys Leu Ile Ser Leu Trp
                140                 145                 150 gga atg gtt ggt cga tct gat gca ttt ttg cat cga gac cta ctg ttc          861
Gly Met Val Gly Arg Ser Asp Ala Phe Leu His Arg Asp Leu Leu Phe
            155                 160                 165 tac aat atg gac acc tat ttt ggt caa tca ggt tct cct gta tta aac          909
Tyr Asn Met Asp Thr Tyr Phe Gly Gln Ser Gly Ser Pro Val Leu Asn
        170                 175                 180 agc gta gat tca atg gtt gcg gtt cat aat gca ggg tat atc gtt ggt          957
Ser Val Asp Ser Met Val Ala Val His Asn Ala Gly Tyr Ile Val Gly
    185                 190                 195 ggt aat agg gaa att aat ggt ggt cct aaa atc aga aga gat ttt aca         1005
Gly Asn Arg Glu Ile Asn Gly Gly Pro Lys Ile Arg Arg Asp Phe Thr
200                 205                 210                 215 aac tta ttt aat caa atg aac                                              1026
Asn Leu Phe Asn Gln Met Asn
                220

<210> SEQ ID NO 4
<211> LENGTH: 342
<212> TYPE: PRT
<213> ORGANISM: Bacillus halmapalus AA513

<400> SEQUENCE: 4

Met  Lys Leu Leu Leu Lys  Leu Thr Phe Val Cys  Ile Phe Met Leu
-120              -115                -110

Ser  Gly Ile Leu Ser Pro  Val Asn Ala Thr Gln  Ala Glu Thr Leu Thr
-105              -100                -95                 -90

Lys Leu Asn Lys Ile Ser Gln Lys Gln Glu Pro Ser Tyr Lys Leu Asp
             -85                 -80                 -75

Glu Glu Met Asp Tyr Val Leu Ile Asp Leu Glu Thr Gln Ser Glu Ser
         -70                 -65                 -60

Ile Ile Ser Ile Gly Asp Asn Thr Asp Leu Gly Asp Gln Ser Phe Thr
        -55                 -50                 -45

Ser Leu Gly Lys Val Gly His Gly Glu Leu Glu Lys Ile Asn Leu Glu
    -40                 -35                 -30

Glu Phe Arg Asn Pro Asn Leu Thr Val Val Asp Pro Leu Thr Arg Lys
-25                 -20                 -15                 -10

Pro Ile Glu Gln Lys Ile Ser Pro Phe Val Val Ile Gly Asp Asp Gly
                 -5                  -1  1                   5

Arg Arg Gln Val Gln Asn Thr Ser Phe Met Pro Phe Arg Ala Leu Thr
            10                  15                  20

Tyr Ile Glu Phe Gly Asn Leu Thr Ser Thr Trp Ser Cys Ser Gly Gly
```

```
                25                  30                  35
Val Ile Gly Thr Asp Leu Val Thr Asn Ala His Cys Val Glu Gly
40                  45                  50                  55

Ser Val Leu Ala Gly Thr Val Pro Gly Met Asn Asn Ser Gln Trp
                60                  65                  70

Ala Tyr Gly His Tyr Arg Val Thr Gln Ile Ile Tyr Pro Asp Gln Tyr
            75                  80                  85

Arg Asn Asn Gly Ala Ser Glu Phe Asp Tyr Ala Ile Leu Arg Val Ala
            90                  95                 100

Pro Asp Ser Asp Gly Arg His Ile Gly Asn Arg Ala Gly Ile Leu Ser
           105                 110                 115

Phe Thr Glu Thr Gly Thr Val Asn Glu Asn Thr Phe Leu Arg Thr Tyr
120                 125                 130                 135

Gly Tyr Pro Gly Asp Lys Ile Ser Glu Thr Lys Leu Ile Ser Leu Trp
                140                 145                 150

Gly Met Val Gly Arg Ser Asp Ala Phe Leu His Arg Asp Leu Leu Phe
            155                 160                 165

Tyr Asn Met Asp Thr Tyr Phe Gly Gln Ser Gly Ser Pro Val Leu Asn
            170                 175                 180

Ser Val Asp Ser Met Val Ala Val His Asn Ala Gly Tyr Ile Val Gly
185                 190                 195

Gly Asn Arg Glu Ile Asn Gly Pro Lys Ile Arg Arg Asp Phe Thr
200                 205                 210                 215

Asn Leu Phe Asn Gln Met Asn
                220

<210> SEQ ID NO 5
<211> LENGTH: 942
<212> TYPE: DNA
<213> ORGANISM: Bacillus licheniformis AC116
<220> FEATURE:
<221> NAME/KEY: CDS
<222> LOCATION: (1)..(942)
<220> FEATURE:
<221> NAME/KEY: sig_peptide
<222> LOCATION: (1)..(87)
<220> FEATURE:
<221> NAME/KEY: pro-peptide
<222> LOCATION: (88)..(276)
<220> FEATURE:
<221> NAME/KEY: mat_peptide
<222> LOCATION: (277)..()

<400> SEQUENCE: 5 atg gcg aaa aat ggt gtt tca cgc gtt ttc att gcc gga ctc atc gga    48
Met Ala Lys Asn Gly Val Ser Arg Val Phe Ile Ala Gly Leu Ile Gly
        -90                 -85                 -80 att tct att ttt tct tcg ggc att tac tct gca caa gct gca tca tcg    96
Ile Ser Ile Phe Ser Ser Gly Ile Tyr Ser Ala Gln Ala Ala Ser Ser
    -75                 -70                 -65 ccg cat acc cca gtc tcc agc gac cct tcg tac aag ccc ggc tcc acc   144
Pro His Thr Pro Val Ser Ser Asp Pro Ser Tyr Lys Pro Gly Ser Thr
-60                 -55                 -50                 -45 tat gat ccc aac ata aaa att gac aat aac ggc gca tat tcg aaa gcc   192
Tyr Asp Pro Asn Ile Lys Ile Asp Asn Asn Gly Ala Tyr Ser Lys Ala
                -40                 -35                 -30 ttc gaa gga acc gga aca ccc ggc ggc tcc gtt cag gcc aaa ccg aaa   240
Phe Glu Gly Thr Gly Thr Pro Gly Gly Ser Val Gln Ala Lys Pro Lys
            -25                 -20                 -15 aaa gaa tcg ccc gcc ggc ccg cct tac agc cct aaa tcg gta atc ggc   288
```

```
                                Lys Glu Ser Pro Ala Gly Pro Pro Tyr Ser Pro Lys Ser Val Ile Gly
                                    -10                 -5                  -1  1 tca gat gaa cgg aca agg gtg act gat aca acg gcc ttt cca tac aga                          336
Ser Asp Glu Arg Thr Arg Val Thr Asp Thr Thr Ala Phe Pro Tyr Arg
 5               10                  15                  20 gca atc gtc cat att tca agc agc atc ggc tca tgc aca ggc tgg ctg                          384
Ala Ile Val His Ile Ser Ser Ser Ile Gly Ser Cys Thr Gly Trp Leu
             25                  30                  35 atc gga ccg aaa acg gta gca acg gcc ggg cac tgc gtc tat gac acg                          432
Ile Gly Pro Lys Thr Val Ala Thr Ala Gly His Cys Val Tyr Asp Thr
         40                  45                  50 gca agc cga tca ttc gcg gga acc gcc acc gtt tcc ccg gga cga aac                          480
Ala Ser Arg Ser Phe Ala Gly Thr Ala Thr Val Ser Pro Gly Arg Asn
     55                  60                  65 ggt tca gct tac cct tac gga tct gtt aca tcg acc cgc tat ttc atc                          528
Gly Ser Ala Tyr Pro Tyr Gly Ser Val Thr Ser Thr Arg Tyr Phe Ile
 70                  75                  80 ccg tcg ggt tgg cag agc gga aat tcc aat tat gac tac gca gcg atc                          576
Pro Ser Gly Trp Gln Ser Gly Asn Ser Asn Tyr Asp Tyr Ala Ala Ile
 85                  90                  95                 100 gag ctc agc cag ccg atc ggc aat acc gtc gga tat ttc gga tat tca                          624
Glu Leu Ser Gln Pro Ile Gly Asn Thr Val Gly Tyr Phe Gly Tyr Ser
             105                 110                 115 tac acc gct tca tcg ctt gca gga gca ggc gtg acc atc agc gga tat                          672
Tyr Thr Ala Ser Ser Leu Ala Gly Ala Gly Val Thr Ile Ser Gly Tyr
         120                 125                 130 cca gga gac aaa aca aca ggc acc cag tgg caa atg tcc gga acg atc                          720
Pro Gly Asp Lys Thr Thr Gly Thr Gln Trp Gln Met Ser Gly Thr Ile
     135                 140                 145 gct gtt tca gaa acg tat aaa ctg caa tat gcg atc gac aca tac gga                          768
Ala Val Ser Glu Thr Tyr Lys Leu Gln Tyr Ala Ile Asp Thr Tyr Gly
 150                 155                 160 ggt caa agc ggt tcc ccg gta tat gag aaa agc agt tca agg aca aac                          816
Gly Gln Ser Gly Ser Pro Val Tyr Glu Lys Ser Ser Ser Arg Thr Asn
165                 170                 175                 180 tgc agc ggc cca tgc tcg ctg gcc gtt cat acg aac ggc gtg tac gga                          864
Cys Ser Gly Pro Cys Ser Leu Ala Val His Thr Asn Gly Val Tyr Gly
             185                 190                 195 gga tcc tct tac aac aga ggc acc cgc att acg aaa gaa gta ttt gat                          912
Gly Ser Ser Tyr Asn Arg Gly Thr Arg Ile Thr Lys Glu Val Phe Asp
         200                 205                 210 aat ttc aca agc tgg aaa aac agc gca cag                                                  942
Asn Phe Thr Ser Trp Lys Asn Ser Ala Gln
     215                 220
```

<210> SEQ ID NO 6
<211> LENGTH: 314
<212> TYPE: PRT
<213> ORGANISM: Bacillus licheniformis AC116

<400> SEQUENCE: 6

```
Met Ala Lys Asn Gly Val Ser Arg Val Phe Ile Ala Gly Leu Ile Gly
                -90                 -85                 -80

Ile Ser Ile Phe Ser Ser Gly Ile Tyr Ser Ala Gln Ala Ala Ser Ser
        -75                 -70                 -65

Pro His Thr Pro Val Ser Ser Asp Pro Ser Tyr Lys Pro Gly Ser Thr
-60                 -55                 -50                 -45

Tyr Asp Pro Asn Ile Lys Ile Asp Asn Asn Gly Ala Tyr Ser Lys Ala
                -40                 -35                 -30
```

```
Phe Glu Gly Thr Gly Thr Pro Gly Gly Ser Val Gln Ala Lys Pro Lys
            -25             -20                     -15

Lys Glu Ser Pro Ala Gly Pro Pro Tyr Ser Pro Lys Ser Val Ile Gly
            -10              -5              -1   1

Ser Asp Glu Arg Thr Arg Val Thr Asp Thr Thr Ala Phe Pro Tyr Arg
 5               10                  15                      20

Ala Ile Val His Ile Ser Ser Ile Gly Ser Cys Thr Gly Trp Leu
                 25                  30                  35

Ile Gly Pro Lys Thr Val Ala Thr Ala Gly His Cys Val Tyr Asp Thr
             40              45                  50

Ala Ser Arg Ser Phe Ala Gly Thr Ala Thr Val Ser Pro Gly Arg Asn
             55              60                  65

Gly Ser Ala Tyr Pro Tyr Gly Ser Val Thr Ser Thr Arg Tyr Phe Ile
 70              75                  80

Pro Ser Gly Trp Gln Ser Gly Asn Ser Asn Tyr Asp Tyr Ala Ala Ile
 85              90                  95                     100

Glu Leu Ser Gln Pro Ile Gly Asn Thr Val Gly Tyr Phe Gly Tyr Ser
                105                 110                 115

Tyr Thr Ala Ser Ser Leu Ala Gly Ala Gly Val Thr Ile Ser Gly Tyr
             120             125                 130

Pro Gly Asp Lys Thr Thr Gly Thr Gln Trp Gln Met Ser Gly Thr Ile
             135             140                 145

Ala Val Ser Glu Thr Tyr Lys Leu Gln Tyr Ala Ile Asp Thr Tyr Gly
 150                 155                 160

Gly Gln Ser Gly Ser Pro Val Tyr Glu Lys Ser Ser Arg Thr Asn
165             170                 175                 180

Cys Ser Gly Pro Cys Ser Leu Ala Val His Thr Asn Gly Val Tyr Gly
             185             190                 195

Gly Ser Ser Tyr Asn Arg Gly Thr Arg Ile Thr Lys Glu Val Phe Asp
             200             205                 210

Asn Phe Thr Ser Trp Lys Asn Ser Ala Gln
             215             220
```

<210> SEQ ID NO 7
<211> LENGTH: 909
<212> TYPE: DNA
<213> ORGANISM: Bacillus pumilus BO32
<220> FEATURE:
<221> NAME/KEY: CDS
<222> LOCATION: (1)..(909)
<220> FEATURE:
<221> NAME/KEY: sig_peptide
<222> LOCATION: (1)..(78)
<220> FEATURE:
<221> NAME/KEY: pro-peptide
<222> LOCATION: (79)..(264)
<220> FEATURE:
<221> NAME/KEY: mat_peptide
<222> LOCATION: (265)..()

<400> SEQUENCE: 7

```
atg atg aaa aag gtg aaa atg tta ctc cct tct cta ctt gtt ttt ggt     48
Met Met Lys Lys Val Lys Met Leu Leu Pro Ser Leu Leu Val Phe Gly
            -85             -80                 -75 gct tta agt gtg cct agt ttt gcc cat gcc gca tct gat tca gtg cta     96
Ala Leu Ser Val Pro Ser Phe Ala His Ala Ala Ser Asp Ser Val Leu
            -70             -65                 -60 acg tct gat tat gac atg gtg act tct gat gga aag gtg atc tct tca    144
Thr Ser Asp Tyr Asp Met Val Thr Ser Asp Gly Lys Val Ile Ser Ser
            -55             -50                 -45
```

```
agt gat ttc cac aat gat acg aaa tcc ccc tca tcc ttt gat aaa gtg      192
Ser Asp Phe His Asn Asp Thr Lys Ser Pro Ser Ser Phe Asp Lys Val
-40             -35                 -30                 -25 gat gat cta tct tca act gtt ggt gaa aaa gta aaa cca cta tca aaa      240
Asp Asp Leu Ser Ser Thr Val Gly Glu Lys Val Lys Pro Leu Ser Lys
            -20                 -15                 -10 tat tta aaa gac ttt caa aca aaa gtc gtc att gga gac gat ggt aga      288
Tyr Leu Lys Asp Phe Gln Thr Lys Val Val Ile Gly Asp Asp Gly Arg
        -5              -1   1               5 aca aaa gta gca aat aca aga gtg gca cca tat aat tca att gct tat      336
Thr Lys Val Ala Asn Thr Arg Val Ala Pro Tyr Asn Ser Ile Ala Tyr
        10              15                  20 act acg ttt ggc ggc tcc agc tgc acg ggg acc ctg att gcc cct aac      384
Thr Thr Phe Gly Gly Ser Ser Cys Thr Gly Thr Leu Ile Ala Pro Asn
25              30                  35                  40 aaa att ttg aca aac gga cac tgc gtg tac aat aca gca tcc aga agt      432
Lys Ile Leu Thr Asn Gly His Cys Val Tyr Asn Thr Ala Ser Arg Ser
            45                  50                  55 tat agt gca aaa gga tcg gtg tat cca ggc atg aat gat agt act gcg      480
Tyr Ser Ala Lys Gly Ser Val Tyr Pro Gly Met Asn Asp Ser Thr Ala
            60                  65                  70 gtg aat ggc tca gca aat atg aca gag ttc tat gta cca agc ggg tat      528
Val Asn Gly Ser Ala Asn Met Thr Glu Phe Tyr Val Pro Ser Gly Tyr
        75                  80                  85 atc aat aca ggt gcg agc caa tat gat ttt gcc gtg atc aaa aca gat      576
Ile Asn Thr Gly Ala Ser Gln Tyr Asp Phe Ala Val Ile Lys Thr Asp
        90                  95                  100 acg aac att ggc aat aca gtt ggt tac cgt tcc atc cgt cag gtg aca      624
Thr Asn Ile Gly Asn Thr Val Gly Tyr Arg Ser Ile Arg Gln Val Thr
105             110                 115                 120 aac tta act ggg aca acg att aaa att tct gga tat cca ggt gat aaa      672
Asn Leu Thr Gly Thr Thr Ile Lys Ile Ser Gly Tyr Pro Gly Asp Lys
            125                 130                 135 atg aga tca act ggc aag atc tcg cag tgg gag atg tca ggt cct gtg      720
Met Arg Ser Thr Gly Lys Ile Ser Gln Trp Glu Met Ser Gly Pro Val
            140                 145                 150 aca aga gaa gat acg aat ctc gca tac tat atg att gat aca ttt agt      768
Thr Arg Glu Asp Thr Asn Leu Ala Tyr Tyr Met Ile Asp Thr Phe Ser
            155                 160                 165 gga aat tca ggc tca gcg atg cta gat caa aat cag caa att gtt ggg      816
Gly Asn Ser Gly Ser Ala Met Leu Asp Gln Asn Gln Gln Ile Val Gly
170             175                 180 gtt cat aac gca ggg tat tca aac ggt acg att aat ggc ggt cca aaa      864
Val His Asn Ala Gly Tyr Ser Asn Gly Thr Ile Asn Gly Gly Pro Lys
185             190                 195                 200 gcg aca gct gcc ttt gtt gaa ttt atc aac tat gca aaa gcg caa          909
Ala Thr Ala Ala Phe Val Glu Phe Ile Asn Tyr Ala Lys Ala Gln
            205                 210                 215

<210> SEQ ID NO 8
<211> LENGTH: 303
<212> TYPE: PRT
<213> ORGANISM: Bacillus pumilus BO32

<400> SEQUENCE: 8

Met Met Lys Lys Val Lys Met Leu Leu Pro Ser Leu Leu Val Phe Gly
                -85                 -80                 -75

Ala Leu Ser Val Pro Ser Phe Ala His Ala Ala Ser Asp Ser Val Leu
        -70                 -65                 -60
```

-continued

```
Thr Ser Asp Tyr Asp Met Val Thr Ser Asp Gly Lys Val Ile Ser Ser
    -55             -50                 -45

Ser Asp Phe His Asn Asp Thr Lys Ser Pro Ser Ser Phe Asp Lys Val
-40             -35                 -30                 -25

Asp Asp Leu Ser Ser Thr Val Gly Glu Lys Val Lys Pro Leu Ser Lys
                -20             -15                 -10

Tyr Leu Lys Asp Phe Gln Thr Lys Val Val Ile Gly Asp Gly Arg
            -5              -1  1               5

Thr Lys Val Ala Asn Thr Arg Val Ala Pro Tyr Asn Ser Ile Ala Tyr
    10              15                  20

Thr Thr Phe Gly Gly Ser Ser Cys Thr Gly Thr Leu Ile Ala Pro Asn
25              30                  35                  40

Lys Ile Leu Thr Asn Gly His Cys Val Tyr Asn Thr Ala Ser Arg Ser
                45                  50                  55

Tyr Ser Ala Lys Gly Ser Val Tyr Pro Gly Met Asn Asp Ser Thr Ala
            60                  65                  70

Val Asn Gly Ser Ala Asn Met Thr Glu Phe Tyr Val Pro Ser Gly Tyr
            75                  80                  85

Ile Asn Thr Gly Ala Ser Gln Tyr Asp Phe Ala Val Ile Lys Thr Asp
    90                  95                  100

Thr Asn Ile Gly Asn Thr Val Gly Tyr Arg Ser Ile Arg Gln Val Thr
105             110                 115                 120

Asn Leu Thr Gly Thr Thr Ile Lys Ile Ser Gly Tyr Pro Gly Asp Lys
                125                 130                 135

Met Arg Ser Thr Gly Lys Ile Ser Gln Trp Glu Met Ser Gly Pro Val
            140                 145                 150

Thr Arg Glu Asp Thr Asn Leu Ala Tyr Tyr Met Ile Asp Thr Phe Ser
    155                 160                 165

Gly Asn Ser Gly Ser Ala Met Leu Asp Gln Asn Gln Gln Ile Val Gly
    170                 175                 180

Val His Asn Ala Gly Tyr Ser Asn Gly Thr Ile Asn Gly Gly Pro Lys
185                 190                 195                 200

Ala Thr Ala Ala Phe Val Glu Phe Ile Asn Tyr Ala Lys Ala Gln
                205                 210                 215

<210> SEQ ID NO 9
<211> LENGTH: 954
<212> TYPE: DNA
<213> ORGANISM: Bacillus licheniformis CDJ31
<220> FEATURE:
<221> NAME/KEY: CDS
<222> LOCATION: (1)..(954)
<220> FEATURE:
<221> NAME/KEY: sig_peptide
<222> LOCATION: (1)..(84)
<220> FEATURE:
<221> NAME/KEY: pro-peptide
<222> LOCATION: (85)..(288)
<220> FEATURE:
<221> NAME/KEY: mat_peptide
<222> LOCATION: (289)..()

<400> SEQUENCE: 9 atg aaa aaa agt gtg aca cgc gta tta atg gcc ggt ctt att gga ata    48
Met Lys Lys Ser Val Thr Arg Val Leu Met Ala Gly Leu Ile Gly Ile
    -95                 -90                 -85 tct att tat tct atg ggc atc gac tcc gct caa gct gca tca tcg ccg    96
Ser Ile Tyr Ser Met Gly Ile Asp Ser Ala Gln Ala Ala Ser Ser Pro
-80             -75                 -70                 -65
```

| | | |
|---|---|---|
| cat act cct gtc tct agc gat cct tca tac aag ccc gac tca tcc gca<br>His Thr Pro Val Ser Ser Asp Pro Ser Tyr Lys Pro Asp Ser Ser Ala<br>　　　　　-60　　　　　　　　　-55　　　　　　　　　-50 | | 144 |
| agc tat gat cct gct att aaa acc aac aaa aac ggc gcc tat tca aaa<br>Ser Tyr Asp Pro Ala Ile Lys Thr Asn Lys Asn Gly Ala Tyr Ser Lys<br>　　　　　-45　　　　　　　　　-40　　　　　　　　　-35 | | 192 |
| gca ttt gaa ggt aca gga aaa cta gac gct ccc ctt tat cag gaa aaa<br>Ala Phe Glu Gly Thr Gly Lys Leu Asp Ala Pro Leu Tyr Gln Glu Lys<br>　　　　　-30　　　　　　　　　-25　　　　　　　　　-20 | | 240 |
| agc aaa cca acc aaa aaa tcc cct gcc gga cca cgt tac agc ccc aaa<br>Ser Lys Pro Thr Lys Lys Ser Pro Ala Gly Pro Arg Tyr Ser Pro Lys<br>　　　　　-15　　　　　　　　　-10　　　　　　　　　 -5　　　　　　　　　-1 | | 288 |
| tcc gtg att ggt tct gat gaa cgg acg aga gtg aca aac act acc gca<br>Ser Val Ile Gly Ser Asp Glu Arg Thr Arg Val Thr Asn Thr Thr Ala<br>1　　　　　　　　　　5　　　　　　　　　10　　　　　　　　　15 | | 336 |
| tat cca tac aga gcg atc gtg cat att tca agc agc atc ggg tct tgc<br>Tyr Pro Tyr Arg Ala Ile Val His Ile Ser Ser Ser Ile Gly Ser Cys<br>　　　　　 20　　　　　　　　　 25　　　　　　　　　 30 | | 384 |
| acc ggc tcc ctg atc ggt ccg aaa acg gtg gca acg gcc gga cac tgc<br>Thr Gly Ser Leu Ile Gly Pro Lys Thr Val Ala Thr Ala Gly His Cys<br>　　　　　 35　　　　　　　　　 40　　　　　　　　　 45 | | 432 |
| att tat gac aca gcg agc ggg tca ttc gcc gga acc gct acc gtt tct<br>Ile Tyr Asp Thr Ala Ser Gly Ser Phe Ala Gly Thr Ala Thr Val Ser<br>　　　　　 50　　　　　　　　　 55　　　　　　　　　 60 | | 480 |
| ccg gga cgg aac ggt tca aca tat ccg tac gga tca gtt aca tca acc<br>Pro Gly Arg Asn Gly Ser Thr Tyr Pro Tyr Gly Ser Val Thr Ser Thr<br>65　　　　　　　　　 70　　　　　　　　　 75　　　　　　　　　 80 | | 528 |
| cgc tat ttc atc ccg tca ggc tat cga agc gga aat tcg aat tac gac<br>Arg Tyr Phe Ile Pro Ser Gly Tyr Arg Ser Gly Asn Ser Asn Tyr Asp<br>　　　　　 85　　　　　　　　　 90　　　　　　　　　 95 | | 576 |
| tac gga gcc ata gag ctc agc cag ccg atc ggc aac acc gtc ggg tat<br>Tyr Gly Ala Ile Glu Leu Ser Gln Pro Ile Gly Asn Thr Val Gly Tyr<br>　　　　　 100　　　　　　　　　 105　　　　　　　　　 110 | | 624 |
| ttc gga tat tcc tac acc acc tcg tct ctc gtt ggg tca agc gtt acc<br>Phe Gly Tyr Ser Tyr Thr Thr Ser Ser Leu Val Gly Ser Ser Val Thr<br>　　　　　 115　　　　　　　　　 120　　　　　　　　　 125 | | 672 |
| atc atc gga tat cca ggc gac aaa aca tcg ggc acc caa tgg cag atg<br>Ile Ile Gly Tyr Pro Gly Asp Lys Thr Ser Gly Thr Gln Trp Gln Met<br>　 130　　　　　　　　　 135　　　　　　　　　 140 | | 720 |
| tcc gga aat atc gcc gtc tca gaa aca tat aaa ctg caa tat gcg atc<br>Ser Gly Asn Ile Ala Val Ser Glu Thr Tyr Lys Leu Gln Tyr Ala Ile<br>145　　　　　　　　　 150　　　　　　　　　 155　　　　　　　　　 160 | | 768 |
| gac aca tac gga ggg cag agc ggc tct ccc gta tat gag gcg agc agc<br>Asp Thr Tyr Gly Gly Gln Ser Gly Ser Pro Val Tyr Glu Ala Ser Ser<br>　　　　　 165　　　　　　　　　 170　　　　　　　　　 175 | | 816 |
| tcc aga acg aat tgc agc ggc cca tgt tcg ctg gcc gtt cat acg aat<br>Ser Arg Thr Asn Cys Ser Gly Pro Cys Ser Leu Ala Val His Thr Asn<br>　　　　　 180　　　　　　　　　 185　　　　　　　　　 190 | | 864 |
| ggg gtg tac gga gga tct tca tac aac aga ggc acc cgg att aca aaa<br>Gly Val Tyr Gly Gly Ser Ser Tyr Asn Arg Gly Thr Arg Ile Thr Lys<br>　 195　　　　　　　　　 200　　　　　　　　　 205 | | 912 |
| gaa gta ttc gat aat ttg aca aac tgg aaa aac agc gcc caa<br>Glu Val Phe Asp Asn Leu Thr Asn Trp Lys Asn Ser Ala Gln<br>　　　　　 210　　　　　　　　　 215　　　　　　　　　 220 | | 954 |

<210> SEQ ID NO 10
<211> LENGTH: 318
<212> TYPE: PRT
<213> ORGANISM: Bacillus licheniformis CDJ31

<400> SEQUENCE: 10

```
Met Lys Lys Ser Val Thr Arg Val Leu Met Ala Gly Leu Ile Gly Ile
    -95              -90              -85
Ser Ile Tyr Ser Met Gly Ile Asp Ser Ala Gln Ala Ala Ser Ser Pro
-80              -75              -70              -65
His Thr Pro Val Ser Ser Asp Pro Ser Tyr Lys Pro Asp Ser Ser Ala
            -60              -55              -50
Ser Tyr Asp Pro Ala Ile Lys Thr Asn Lys Asn Gly Ala Tyr Ser Lys
            -45              -40              -35
Ala Phe Glu Gly Thr Gly Lys Leu Asp Ala Pro Leu Tyr Gln Glu Lys
            -30              -25              -20
Ser Lys Pro Thr Lys Lys Ser Pro Ala Gly Pro Arg Tyr Ser Pro Lys
    -15              -10                       -5              -1
Ser Val Ile Gly Ser Asp Glu Arg Thr Arg Val Thr Asn Thr Thr Ala
1                5                       10                  15
Tyr Pro Tyr Arg Ala Ile Val His Ile Ser Ser Ile Gly Ser Cys
            20              25                       30
Thr Gly Ser Leu Ile Gly Pro Lys Thr Val Ala Thr Ala Gly His Cys
            35              40                       45
Ile Tyr Asp Thr Ala Ser Gly Ser Phe Ala Gly Thr Ala Thr Val Ser
50              55                       60
Pro Gly Arg Asn Gly Ser Thr Tyr Pro Tyr Gly Ser Val Thr Ser Thr
65              70                       75                  80
Arg Tyr Phe Ile Pro Ser Gly Tyr Arg Ser Gly Asn Ser Asn Tyr Asp
            85                       90                  95
Tyr Gly Ala Ile Glu Leu Ser Gln Pro Ile Gly Asn Thr Val Gly Tyr
            100              105                       110
Phe Gly Tyr Ser Tyr Thr Thr Ser Ser Leu Val Gly Ser Ser Val Thr
            115              120                       125
Ile Ile Gly Tyr Pro Gly Asp Lys Thr Ser Gly Thr Gln Trp Gln Met
    130              135                       140
Ser Gly Asn Ile Ala Val Ser Glu Thr Tyr Lys Leu Gln Tyr Ala Ile
145              150                       155                  160
Asp Thr Tyr Gly Gly Gln Ser Gly Ser Pro Val Tyr Glu Ala Ser Ser
            165                       170                  175
Ser Arg Thr Asn Cys Ser Gly Pro Cys Ser Leu Ala Val His Thr Asn
            180                       185                  190
Gly Val Tyr Gly Gly Ser Ser Tyr Asn Arg Gly Thr Arg Ile Thr Lys
            195                       200                  205
Glu Val Phe Asp Asn Leu Thr Asn Trp Lys Asn Ser Ala Gln
    210                       215                  220

<210> SEQ ID NO 11
<211> LENGTH: 906
<212> TYPE: DNA
<213> ORGANISM: Bacillus pumilus JA96
<220> FEATURE:
<221> NAME/KEY: CDS
<222> LOCATION: (1)..(906)
<220> FEATURE:
<221> NAME/KEY: sig_peptide
<222> LOCATION: (1)..(75)
<220> FEATURE:
<221> NAME/KEY: pro-peptide
<222> LOCATION: (76)..(261)
<220> FEATURE:
<221> NAME/KEY: mat_peptide
<222> LOCATION: (262)..()
```

<400> SEQUENCE: 11

| | | |
|---|---|---|
| atg aaa aag gtg aaa aaa tta atc cct tct cta ctc gtt ttt ggt gct<br>Met Lys Lys Val Lys Lys Leu Ile Pro Ser Leu Leu Val Phe Gly Ala<br>    -85            -80                -75 | | 48 |
| tta agt gtg cct agt ttt gcc cat gca gca tct gat tca gta ctt acg<br>Leu Ser Val Pro Ser Phe Ala His Ala Ala Ser Asp Ser Val Leu Thr<br>-70                -65                -60 | | 96 |
| tct gat tat gac atg gtg act tct gac gga aag gta att tct tca gct<br>Ser Asp Tyr Asp Met Val Thr Ser Asp Gly Lys Val Ile Ser Ser Ala<br>-55            -50                -45                -40 | | 144 |
| gac ttc cac aac gat atg aaa acc ccc tca tcc ttt gac aaa gtg gat<br>Asp Phe His Asn Asp Met Lys Thr Pro Ser Ser Phe Asp Lys Val Asp<br>                -35                -30                -25 | | 192 |
| gat ctc tct tct act att ggc gaa aaa gta aaa cca ctc aca aca tat<br>Asp Leu Ser Ser Thr Ile Gly Glu Lys Val Lys Pro Leu Thr Thr Tyr<br>            -20                -15                -10 | | 240 |
| tta aaa gac ttt caa aca aaa gta gtc att gga gac gat ggt aga aca<br>Leu Lys Asp Phe Gln Thr Lys Val Val Ile Gly Asp Asp Gly Arg Thr<br>    -5                -1   1                 5 | | 288 |
| aaa gtg acg aat aca aga gta gca ccc tat aat tct att gct tat att<br>Lys Val Thr Asn Thr Arg Val Ala Pro Tyr Asn Ser Ile Ala Tyr Ile<br>10                15                20                25 | | 336 |
| aca ttt ggt gga tct agc tgc act gga aca ctc att gct cca aac aaa<br>Thr Phe Gly Gly Ser Ser Cys Thr Gly Thr Leu Ile Ala Pro Asn Lys<br>                30                35                40 | | 384 |
| ata ttg aca aac gga cac tgc gtc tac aat aca gcc aca aga agt tat<br>Ile Leu Thr Asn Gly His Cys Val Tyr Asn Thr Ala Thr Arg Ser Tyr<br>            45                50                55 | | 432 |
| agt gca aaa ggg tct gtc tac cca ggc atg aat gac agc acg gct gtg<br>Ser Ala Lys Gly Ser Val Tyr Pro Gly Met Asn Asp Ser Thr Ala Val<br>        60                65                70 | | 480 |
| aac ggc tca gca aac atg acc gaa ttc tat gta cca agc gga tat atc<br>Asn Gly Ser Ala Asn Met Thr Glu Phe Tyr Val Pro Ser Gly Tyr Ile<br>75                80                85 | | 528 |
| aac acg ggg gcg agt caa tat gat ttt gcc gtc att aaa aca gat acg<br>Asn Thr Gly Ala Ser Gln Tyr Asp Phe Ala Val Ile Lys Thr Asp Thr<br>90                95                100                105 | | 576 |
| aac att gga aat acg gtc ggc tat cgc tct att cgt caa gtg aca aat<br>Asn Ile Gly Asn Thr Val Gly Tyr Arg Ser Ile Arg Gln Val Thr Asn<br>            110                115                120 | | 624 |
| cta aca ggt aca acg att aaa att tct gga tat cca ggt gat aaa atg<br>Leu Thr Gly Thr Thr Ile Lys Ile Ser Gly Tyr Pro Gly Asp Lys Met<br>        125                130                135 | | 672 |
| aga tcg act ggc aaa gtg tca caa tgg gaa atg tca ggt cca gtc acg<br>Arg Ser Thr Gly Lys Val Ser Gln Trp Glu Met Ser Gly Pro Val Thr<br>    140                145                150 | | 720 |
| aga gaa gat acg aat ctc gca tac tat acg atc gat aca ttt agc gga<br>Arg Glu Asp Thr Asn Leu Ala Tyr Tyr Thr Ile Asp Thr Phe Ser Gly<br>155                160                165 | | 768 |
| aac tct ggc tct gcg atg cta gat cag aac caa caa atc gtc ggg gtc<br>Asn Ser Gly Ser Ala Met Leu Asp Gln Asn Gln Gln Ile Val Gly Val<br>170                175                180                185 | | 816 |
| cat aat gcg ggt tat tca aat gga acg atc aac ggt gga cca aaa gcg<br>His Asn Ala Gly Tyr Ser Asn Gly Thr Ile Asn Gly Gly Pro Lys Ala<br>            190                195                200 | | 864 |
| act gct gcc ttt gtt gaa ttt atc aac tat gcg aag gcg caa<br>Thr Ala Ala Phe Val Glu Phe Ile Asn Tyr Ala Lys Ala Gln<br>        205                210                215 | | 906 |

<210> SEQ ID NO 12
<211> LENGTH: 302
<212> TYPE: PRT
<213> ORGANISM: Bacillus pumilus JA96

<400> SEQUENCE: 12

```
Met Lys Lys Val Lys Lys Leu Ile Pro Ser Leu Leu Val Phe Gly Ala
        -85                 -80                 -75
Leu Ser Val Pro Ser Phe Ala His Ala Ser Asp Ser Val Leu Thr
    -70                 -65                 -60
Ser Asp Tyr Asp Met Val Thr Ser Asp Gly Lys Val Ile Ser Ser Ala
-55                 -50                 -45                 -40
Asp Phe His Asn Asp Met Lys Thr Pro Ser Ser Phe Asp Lys Val Asp
                -35                 -30                 -25
Asp Leu Ser Ser Thr Ile Gly Glu Lys Val Lys Pro Leu Thr Thr Tyr
            -20                 -15                 -10
Leu Lys Asp Phe Gln Thr Lys Val Val Ile Gly Asp Asp Gly Arg Thr
        -5                  -1   1                5
Lys Val Thr Asn Thr Arg Val Ala Pro Tyr Asn Ser Ile Ala Tyr Ile
10                  15                  20                  25
Thr Phe Gly Gly Ser Ser Cys Thr Gly Thr Leu Ile Ala Pro Asn Lys
                30                  35                  40
Ile Leu Thr Asn Gly His Cys Val Tyr Asn Thr Ala Thr Arg Ser Tyr
            45                  50                  55
Ser Ala Lys Gly Ser Val Tyr Pro Gly Met Asn Asp Ser Thr Ala Val
        60                  65                  70
Asn Gly Ser Ala Asn Met Thr Glu Phe Tyr Val Pro Ser Gly Tyr Ile
75                  80                  85
Asn Thr Gly Ala Ser Gln Tyr Asp Phe Ala Val Ile Lys Thr Asp Thr
90                  95                  100                 105
Asn Ile Gly Asn Thr Val Gly Tyr Arg Ser Ile Arg Gln Val Thr Asn
                110                 115                 120
Leu Thr Gly Thr Thr Ile Lys Ile Ser Gly Tyr Pro Gly Asp Lys Met
            125                 130                 135
Arg Ser Thr Gly Lys Val Ser Gln Trp Glu Met Ser Gly Pro Val Thr
        140                 145                 150
Arg Glu Asp Thr Asn Leu Ala Tyr Tyr Thr Ile Asp Thr Phe Ser Gly
        155                 160                 165
Asn Ser Gly Ser Ala Met Leu Asp Gln Asn Gln Ile Val Gly Val
170                 175                 180                 185
His Asn Ala Gly Tyr Ser Asn Gly Thr Ile Asn Gly Gly Pro Lys Ala
                190                 195                 200
Thr Ala Ala Phe Val Glu Phe Ile Asn Tyr Ala Lys Ala Gln
            205                 210                 215
```

<210> SEQ ID NO 13
<211> LENGTH: 939
<212> TYPE: DNA
<213> ORGANISM: Bacillus subtilis IS75
<220> FEATURE:
<221> NAME/KEY: CDS
<222> LOCATION: (1)..(939)
<220> FEATURE:
<221> NAME/KEY: pro-peptide
<222> LOCATION: (103)..(279)
<220> FEATURE:
<221> NAME/KEY: mat_peptide
<222> LOCATION: (280)..()

<400> SEQUENCE: 13

```
atg aaa tta gtt cca aga ttc aga aaa caa tgg ttc gct tac tta acg         48
Met Lys Leu Val Pro Arg Phe Arg Lys Gln Trp Phe Ala Tyr Leu Thr
            -90                 -85                 -80 gtt ttg tgt ttg gct ttg gca gca gcg gtt tct ttt ggc gta ccg gca         96
Val Leu Cys Leu Ala Leu Ala Ala Ala Val Ser Phe Gly Val Pro Ala
        -75                 -70                 -65 aaa gcg gca gag aac ccg caa act tct gta tcg aat acc ggt aaa gaa        144
Lys Ala Ala Glu Asn Pro Gln Thr Ser Val Ser Asn Thr Gly Lys Glu
    -60                 -55                 -50 gct gat gct acg aaa aac caa acg tca aaa gca gat cag gtt tcc gcc        192
Ala Asp Ala Thr Lys Asn Gln Thr Ser Lys Ala Asp Gln Val Ser Ala
-45                 -40                 -35                 -30 cct tat gag gga acc gga aaa aca agt aaa tcg tta tac ggc ggc caa        240
Pro Tyr Glu Gly Thr Gly Lys Thr Ser Lys Ser Leu Tyr Gly Gly Gln
                -25                 -20                 -15 acg gaa ctg gaa aaa aac att caa acc tta cag cct tcg agc att atc        288
Thr Glu Leu Glu Lys Asn Ile Gln Thr Leu Gln Pro Ser Ser Ile Ile
            -10                 -5                  -1  1 gga act gat gaa cgc acc aga atc tcc agc acg aca tct ttt cca tat        336
Gly Thr Asp Glu Arg Thr Arg Ile Ser Ser Thr Thr Ser Phe Pro Tyr
    5                   10                  15 aga gca acc gtt caa ctg tca atc aag tat ccc aac act tca agc act        384
Arg Ala Thr Val Gln Leu Ser Ile Lys Tyr Pro Asn Thr Ser Ser Thr
20                  25                  30                  35 tat gga tgt acc gga ttt tta gtc aat cca aat aca gtc gtc acg gct        432
Tyr Gly Cys Thr Gly Phe Leu Val Asn Pro Asn Thr Val Val Thr Ala
                40                  45                  50 gga cat tgt gtg tac agc cag gat cat gga tgg gct tcg acg ata acc        480
Gly His Cys Val Tyr Ser Gln Asp His Gly Trp Ala Ser Thr Ile Thr
        55                  60                  65 gcc gcg ccg ggc cgc aat ggt tcg tca tat ccg tac ggt act tat tca        528
Ala Ala Pro Gly Arg Asn Gly Ser Ser Tyr Pro Tyr Gly Thr Tyr Ser
    70                  75                  80 ggc acg atg ttt tac tcc gtc aaa gga tgg acg gaa agc aaa gac acc        576
Gly Thr Met Phe Tyr Ser Val Lys Gly Trp Thr Glu Ser Lys Asp Thr
85                  90                  95 aac tat gat tac gga gct att aaa tta aac ggt tct cct gga aac acg        624
Asn Tyr Asp Tyr Gly Ala Ile Lys Leu Asn Gly Ser Pro Gly Asn Thr
100                 105                 110                 115 gtt ggc tgg tac ggc tac cgg act aca aac agc agc agt ccc gtg ggc        672
Val Gly Trp Tyr Gly Tyr Arg Thr Thr Asn Ser Ser Ser Pro Val Gly
                120                 125                 130 ctt tcc tcg tca gtg aca gga ttc cca tgt gac aaa acc ttt ggc acg        720
Leu Ser Ser Ser Val Thr Gly Phe Pro Cys Asp Lys Thr Phe Gly Thr
        135                 140                 145 atg tgg tct gat aca aag ccg att cgc tcc gct gaa acg tat aag ctg        768
Met Trp Ser Asp Thr Lys Pro Ile Arg Ser Ala Glu Thr Tyr Lys Leu
    150                 155                 160 acc tat aca acc gat acg tac ggc tgc caa agc ggc tcg cct gtt tat        816
Thr Tyr Thr Thr Asp Thr Tyr Gly Cys Gln Ser Gly Ser Pro Val Tyr
165                 170                 175 cga aac tac agt gat aca ggg cag aca gct att gcc att cac acg aac        864
Arg Asn Tyr Ser Asp Thr Gly Gln Thr Ala Ile Ala Ile His Thr Asn
180                 185                 190                 195 gga gga tcg tca tat aac ttg gga aca agg gtg acg aac gat gta ttc        912
Gly Gly Ser Ser Tyr Asn Leu Gly Thr Arg Val Thr Asn Asp Val Phe
                200                 205                 210 aac aat att caa tat tgg gca aat caa                                    939
Asn Asn Ile Gln Tyr Trp Ala Asn Gln
```

-continued

```
Asn Asn Ile Gln Tyr Trp Ala Asn Gln
            215             220

<210> SEQ ID NO 14
<211> LENGTH: 313
<212> TYPE: PRT
<213> ORGANISM: Bacillus subtilis IS75

<400> SEQUENCE: 14

Met Lys Leu Val Pro Arg Phe Arg Lys Gln Trp Phe Ala Tyr Leu Thr
            -90              -85              -80

Val Leu Cys Leu Ala Leu Ala Ala Val Ser Phe Gly Val Pro Ala
            -75              -70              -65

Lys Ala Ala Glu Asn Pro Gln Thr Ser Val Ser Asn Thr Gly Lys Glu
    -60              -55              -50

Ala Asp Ala Thr Lys Asn Gln Thr Ser Lys Ala Asp Gln Val Ser Ala
-45              -40              -35              -30

Pro Tyr Glu Gly Thr Gly Lys Thr Ser Lys Ser Leu Tyr Gly Gly Gln
                -25              -20              -15

Thr Glu Leu Glu Lys Asn Ile Gln Thr Leu Gln Pro Ser Ser Ile Ile
            -10              -5               -1  1

Gly Thr Asp Glu Arg Thr Arg Ile Ser Ser Thr Ser Phe Pro Tyr
    5                10               15

Arg Ala Thr Val Gln Leu Ser Ile Lys Tyr Pro Asn Thr Ser Ser Thr
20               25               30               35

Tyr Gly Cys Thr Gly Phe Leu Val Asn Pro Asn Thr Val Val Thr Ala
                40               45               50

Gly His Cys Val Tyr Ser Gln Asp His Gly Trp Ala Ser Thr Ile Thr
                55               60               65

Ala Ala Pro Gly Arg Asn Gly Ser Ser Tyr Pro Tyr Gly Thr Tyr Ser
            70               75               80

Gly Thr Met Phe Tyr Ser Val Lys Gly Trp Thr Glu Ser Lys Asp Thr
    85               90               95

Asn Tyr Asp Tyr Gly Ala Ile Lys Leu Asn Gly Ser Pro Gly Asn Thr
100              105              110              115

Val Gly Trp Tyr Gly Tyr Arg Thr Thr Asn Ser Ser Ser Pro Val Gly
                120              125              130

Leu Ser Ser Val Thr Gly Phe Pro Cys Asp Lys Thr Phe Gly Thr
            135              140              145

Met Trp Ser Asp Thr Lys Pro Ile Arg Ser Ala Glu Thr Tyr Lys Leu
    150              155              160

Thr Tyr Thr Thr Asp Thr Tyr Gly Cys Gln Ser Gly Ser Pro Val Tyr
    165              170              175

Arg Asn Tyr Ser Asp Thr Gly Gln Thr Ala Ile Ala Ile His Thr Asn
180              185              190              195

Gly Gly Ser Ser Tyr Asn Leu Gly Thr Arg Val Thr Asn Asp Val Phe
                200              205              210

Asn Asn Ile Gln Tyr Trp Ala Asn Gln
            215             220
```